(12) United States Patent
Kohno et al.

(10) Patent No.: US 8,580,758 B2
(45) Date of Patent: Nov. 12, 2013

(54) METHOD OF INHIBITING CANCER CELL PROLIFERATION, PROLIFERATION INHIBITOR AND SCREENING METHOD

(75) Inventors: Kimitoshi Kohno, Kitakyushu (JP); Hiroto Izumi, Kitakyushu (JP); Yasuyuki Sasaguri, Kitakyushu (JP)

(73) Assignee: University of Occupational and Environmental Health, Japan, Kitakyushu-shi, Fukuoka (JP)

( * ) Notice: Subject to any disclaimer, the term of this patent is extended or adjusted under 35 U.S.C. 154(b) by 334 days.

(21) Appl. No.: 12/810,696

(22) PCT Filed: Dec. 26, 2008

(86) PCT No.: PCT/JP2008/073817
§ 371 (c)(1),
(2), (4) Date: Jun. 25, 2010

(87) PCT Pub. No.: WO2009/084668
PCT Pub. Date: Jul. 9, 2009

(65) Prior Publication Data
US 2010/0280101 A1 Nov. 4, 2010

(30) Foreign Application Priority Data
Dec. 28, 2007 (JP) .................................. 2007-341430

(51) Int. Cl.
*A61K 48/00* (2006.01)
*C12N 15/11* (2006.01)
*C07H 21/02* (2006.01)
*C07H 21/04* (2006.01)

(52) U.S. Cl.
USPC ...................................................... 514/44 A

(58) Field of Classification Search
USPC ............................................ 514/44; 536/24.5
See application file for complete search history.

(56) References Cited

FOREIGN PATENT DOCUMENTS

| | | | |
|---|---|---|---|
| JP | 2002-536420 A | 10/2002 | |
| JP | 2005-527553 A | 9/2005 | |
| JP | 2006-506964 A | 3/2006 | |
| WO | WO 00/47231 A2 | 8/2000 | |
| WO | WO 03/082269 A1 | 10/2003 | |
| WO | WO 03/105761 A2 | 12/2003 | |
| WO | 2004/051269 A | 6/2004 | |

OTHER PUBLICATIONS

Izumi et al. Cancer Sci., Dec. 2010 vol. 101:2538-2545.*
Basaki et al., *European Journal of Cancer*, doi:10.1016/j.ejca.2009.12.024 (2010).
Eckerdt et al., *Cancer Research*, 66(14): 6895-6898 (Jul. 15, 2006).
Ishiguchi et al., *Int. J. Cancer*, 111: 900-909 (2004).

(Continued)

Primary Examiner — Terra Cotta Gibbs
(74) Attorney, Agent, or Firm — Leydig, Voit & Mayer, Ltd.

(57) ABSTRACT

The present invention provides a method of inhibiting cancer cell proliferation by suppressing a function of ZNF143, a cancer cell proliferation inhibitor containing as an active ingredient a substance capable of inhibiting a function of ZNF143, like a ZNF143-specific siRNA, a prophylactic and/or therapeutic drug for cancer, a method of detecting cancer cells, a diagnostic reagent for cancer, a vector and transformant cell incorporating the vector, and a screening method for a substance possessing cancer cell proliferation inhibitory activity with the amount of inhibition of the binding of ZNF143 protein as an index.

16 Claims, 3 Drawing Sheets

| Related to nucleic acids or chromatin | Related to cell division | Related to cell cycle | Related to transcriptional factors |
|---|---|---|---|
| | Stathmin1 | MCM2・3・4・5・7・10 | UHRF1 |
| LaminB1 | SPBC25 | CyclinA2・E2・F | ZNF367 |
| H1X | CNAP1 | AURKB | |
| H2AX | BUB1 | CDC6 | Others |
| H1O | BRRN1 | PLK1 | CCNE2 |
| HMGB2/B3 | DTL | WEE1 | CCNF |
| CENPA | GTSE1 | CDCA3・4・5・8 | BIRC5(Survivin) |
| CENPH | CEP2 | CDC20 | ESPL1 |
| CBX5・6 | | CDC2L6 | CDK2 |
| NASP | Related to DNA synthesis | CDKN2C | CCNA2 |
| | PFS1・2 | | |
| | CDT1 | | |
| | RFC2・4 | | |
| | TS | | |

(56) References Cited

OTHER PUBLICATIONS

Myslinski et al., *The Journal of Biological Chemistry*, 281(52): 39953-39962 (Dec. 29, 2006).
Myslinski et al., *Nucleic Acids Research*, 35(10): 3453-3464 (2007).
Schuster et al., *The EMBO Journal*, 14(15): 3777-3787 (1995).
Torigoe et al., *Curr. Med. Chem.—Anti-Cancer Agents*, 5: 15-27 (2005).
Wakasugi et al., *Oncogene*, 26: 5194-5203 (2007).
Chen et al., *Stem Cells*, 26(11): 2759-2767 (2008).
Gao et al., *Academic Journal of Second Military Medical University*, 29(7): 756-761 (2008).
Kubota et al., *The Journal of Biological Chemistry*, 275(37): 28641-28648 (2000).
Myslinski et al., *The Journal of Biological Chemistry*, 273(34): 21998-22006 (1998).
Rincon et al., *Nucleic Acids Research*, 26(21): 4846-4856 (1998).
Tommerup et at., *Genomics*, 27(2): 259-264 (1995).
European Patent Office, Extended European Search Report in European Patent Application No. 08869206.6 (Dec. 5, 2012).

\* cited by examiner

FIG. 1

| Related to nucleic acids or chromatin | Related to cell division | Related to cell cycle | Related to transcriptional factors |
|---|---|---|---|
|  | Stathmin1 | MCM2・3・4・5・7・10 | UHRF1 |
| LaminB1 | SPBC25 | CyclinA2・E2・F | ZNF367 |
| H1X | CNAP1 | AURKB |  |
| H2AX | BUB1 | CDC6 | Others |
| H1O | BRRN1 | PLK1 | CCNE2 |
| HMGB2/B3 | DTL | WEE1 | CCNF |
| CENPA | GTSE1 | CDCA3・4・5・8 | BIRC5(Survivin) |
| CENPH | CEP2 | CDC20 | ESPL1 |
| CBX5・6 |  | CDC2L6 | CDK2 |
| NASP | Related to DNA synthesis | CDKN2C | CCNA2 |
|  | PFS1・2 |  |  |
|  | CDT1 |  |  |
|  | RFC2・4 |  |  |
|  | TS |  |  |

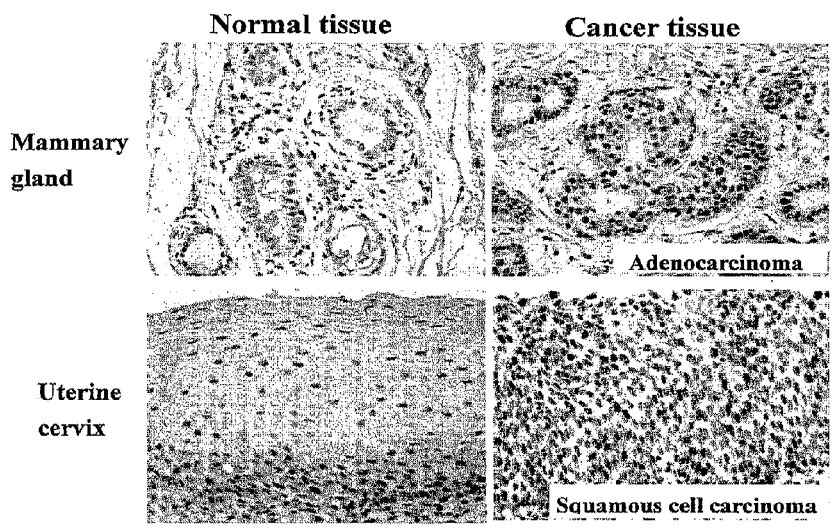

FIG. 2

SEQUENCE LISTING

<160> NUMBER OF SEQ ID NOS: 44

<210> SEQ ID NO 1
<211> LENGTH: 25
<212> TYPE: RNA
<213> ORGANISM: Homo sapiens

<400> SEQUENCE: 1
uaaccauagc aacagagugc guucc           25

<210> SEQ ID NO 2
<211> LENGTH: 25
<212> TYPE: RNA
<213> ORGANISM: Homo sapiens

<400> SEQUENCE: 2
uaauuuguug cacuggcaaa ugccc           25

<210> SEQ ID NO 3
<211> LENGTH: 25
<212> TYPE: RNA
<213> ORGANISM: Homo sapiens

```
<400> SEQUENCE: 3
auaagcugug guaccaucuu ccagc                                          25

<210> SEQ ID NO 4
<211> LENGTH: 19
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 4
yywcccrnmn tssnyyrcr                                                 19

<210> SEQ ID NO 5
<211> LENGTH: 69
<212> TYPE: DNA
<213> ORGANISM: Homo sapiens

<400> SEQUENCE: 5
acgcgtacta cgcctcccag cgtgctttgc ggcgggccgg ccactacgcc tcccagcgtg    60
ctttgcggc                                                            69

<210> SEQ ID NO 6
<211> LENGTH: 2946
<212> TYPE: DNA
<213> ORGANISM: Homo sapiens
<220> FEATURE:
<221> NAME/KEY: CDS
<222> LOCATION: (119)..(2035)

<400> SEQUENCE: 6
ggcgggcctc agacacacta tgcgggttgc ggggcctggg ggccggacgg ctgtttcctg    60
tcctggtgca tggtggtcgg acgaaggaat tgttggaaaa ttttctcgga ggtagaag     118 atg ttg tta gcc caa ata aat cga gat tct cag gga atg aca gag ttt   166
Met Leu Leu Ala Gln Ile Asn Arg Asp Ser Gln Gly Met Thr Glu Phe
 1               5                  10                  15 cct gga gga ggg atg gag gcg caa cat gtt acg ctg tgc ttg aca gag   214
Pro Gly Gly Gly Met Glu Ala Gln His Val Thr Leu Cys Leu Thr Glu
                 20                  25                  30 gca gtc acc gtg gca gat ggt gac aac tta gaa aat atg gaa ggc gta   262
Ala Val Thr Val Ala Asp Gly Asp Asn Leu Glu Asn Met Glu Gly Val
             35                  40                  45 agc ttg caa gca gta aca ctt gca gat ggt tct act gct tac ata caa   310
Ser Leu Gln Ala Val Thr Leu Ala Asp Gly Ser Thr Ala Tyr Ile Gln
         50                  55                  60 cac aat tct aaa gat gca aaa ctc ata gat ggc cag gtc att cag ttg   358
His Asn Ser Lys Asp Ala Lys Leu Ile Asp Gly Gln Val Ile Gln Leu
 65                  70                  75                  80 gaa gat ggt tct gcg gcc tat gtt caa cat gta ccc ata cct aaa agt   406
Glu Asp Gly Ser Ala Ala Tyr Val Gln His Val Pro Ile Pro Lys Ser
                 85                  90                  95 aca ggg gac agt ttg cgt cta gag gat ggt caa gca gta cag tta gaa   454
Thr Gly Asp Ser Leu Arg Leu Glu Asp Gly Gln Ala Val Gln Leu Glu
```

```
                100                 105                 110
gat ggt acc aca gca ttt att cac cac acc tcc aaa gat agt tat gac      502
Asp Gly Thr Thr Ala Phe Ile His His Thr Ser Lys Asp Ser Tyr Asp
        115                 120                 125 cag agt gca tta cag gcg gtt cag ctg gaa gat ggt acc aca gct tat      550
Gln Ser Ala Leu Gln Ala Val Gln Leu Glu Asp Gly Thr Thr Ala Tyr
    130                 135                 140 atc cac cat gca gtg caa gtc ccg cag tct gac acc atc ttg gca att      598
Ile His His Ala Val Gln Val Pro Gln Ser Asp Thr Ile Leu Ala Ile
145                 150                 155                 160 cag gct gat ggg aca gtg gca ggt ctg cac act ggg gat gct aca att      646
Gln Ala Asp Gly Thr Val Ala Gly Leu His Thr Gly Asp Ala Thr Ile
                165                 170                 175 gac cct gac acc atc agt gct ttg gaa cag tat gca gca aag gtg tcc      694
Asp Pro Asp Thr Ile Ser Ala Leu Glu Gln Tyr Ala Ala Lys Val Ser
            180                 185                 190 att gat gga agt gaa agt gta gca ggt act gga atg att gga gaa aat      742
Ile Asp Gly Ser Glu Ser Val Ala Gly Thr Gly Met Ile Gly Glu Asn
        195                 200                 205 gag caa gag aaa aaa atg cag att gtt tta caa gga cat gct aca aga      790
Glu Gln Glu Lys Lys Met Gln Ile Val Leu Gln Gly His Ala Thr Arg
    210                 215                 220 gta act gct aaa tct caa cag agt gga gag aag gca ttt cga tgt gaa      838
Val Thr Ala Lys Ser Gln Gln Ser Gly Glu Lys Ala Phe Arg Cys Glu
225                 230                 235                 240 tat gat gga tgt gga aaa tta tat aca aca gct cat cat ctc aag gtc      886
Tyr Asp Gly Cys Gly Lys Leu Tyr Thr Thr Ala His His Leu Lys Val
                245                 250                 255 cat gag agg tca cac aca gga gat cgg cct tat cag tgt gag cat gca      934
His Glu Arg Ser His Thr Gly Asp Arg Pro Tyr Gln Cys Glu His Ala
            260                 265                 270 ggc tgt ggg aag gca ttt gca aca ggt tat gga tta aaa agt cac gtc      982
Gly Cys Gly Lys Ala Phe Ala Thr Gly Tyr Gly Leu Lys Ser His Val
        275                 280                 285 aga act cat aca gga gaa aag cca tat cgg tgt tcg gaa gat aat tgt     1030
Arg Thr His Thr Gly Glu Lys Pro Tyr Arg Cys Ser Glu Asp Asn Cys
    290                 295                 300 act aaa tct ttc aaa act tca gga gat cta cag aaa cac atc aga act     1078
Thr Lys Ser Phe Lys Thr Ser Gly Asp Leu Gln Lys His Ile Arg Thr
305                 310                 315                 320 cat aca gga gaa agg ccc ttt aag tgt ccc ttc gaa ggc tgc ggt cgg     1126
His Thr Gly Glu Arg Pro Phe Lys Cys Pro Phe Glu Gly Cys Gly Arg
                325                 330                 335 tcc ttt aca aca tca aat atc aga aaa gtg cac gtt agg aca cac aca     1174
Ser Phe Thr Thr Ser Asn Ile Arg Lys Val His Val Arg Thr His Thr
            340                 345                 350 gga gaa aga cct tat tac tgc aca gag cca gga tgt ggg agg gca ttt     1222
Gly Glu Arg Pro Tyr Tyr Cys Thr Glu Pro Gly Cys Gly Arg Ala Phe
        355                 360                 365 gcc agt gca aca aat tat aaa aac cat gtg agg ata cac aca gga gaa     1270
Ala Ser Ala Thr Asn Tyr Lys Asn His Val Arg Ile His Thr Gly Glu
    370                 375                 380 aag cca tat gtt tgt aca gtt cct ggg tgt gac aaa agg ttt aca gaa     1318
Lys Pro Tyr Val Cys Thr Val Pro Gly Cys Asp Lys Arg Phe Thr Glu
385                 390                 395                 400 tat tcc agt ttg tac aaa cat cat gtt gtc cac act cat tcc aaa cct     1366
Tyr Ser Ser Leu Tyr Lys His His Val Val His Thr His Ser Lys Pro
                405                 410                 415 tac aac tgt aac cac tgt ggg aag aca tac aag cag atc tcc acg ctg     1414
Tyr Asn Cys Asn His Cys Gly Lys Thr Tyr Lys Gln Ile Ser Thr Leu
```

-continued

```
                    420                 425                 430
gcc atg cac aaa cgg aca gcc cac aac gac act gag ccc atc gag gag      1462
Ala Met His Lys Arg Thr Ala His Asn Asp Thr Glu Pro Ile Glu Glu
        435                 440                 445 gag cag gaa gcc ttc ttt gag ccg ccc cca ggt caa ggt gaa gat gtt      1510
Glu Gln Glu Ala Phe Phe Glu Pro Pro Pro Gly Gln Gly Glu Asp Val
450                 455                 460 ctt aaa ggg tcc cag att acg tat gtt aca ggt gta gaa ggg gac gac      1558
Leu Lys Gly Ser Gln Ile Thr Tyr Val Thr Gly Val Glu Gly Asp Asp
465                 470                 475                 480 gtt gtt tct aca caa gta gcc aca gta acc caa tct gga ctg agt caa      1606
Val Val Ser Thr Gln Val Ala Thr Val Thr Gln Ser Gly Leu Ser Gln
                485                 490                 495 caa gtt aca ctc ata tcc cag gat ggg act cag cat gtc aac ata tct      1654
Gln Val Thr Leu Ile Ser Gln Asp Gly Thr Gln His Val Asn Ile Ser
            500                 505                 510 caa gct gac atg cag gcc att ggc aac acc atc aca atg gta acg cag      1702
Gln Ala Asp Met Gln Ala Ile Gly Asn Thr Ile Thr Met Val Thr Gln
        515                 520                 525 gat ggc acg ccc atc aca gtc ccc gcc cat gat gca gtc atc tcc tca      1750
Asp Gly Thr Pro Ile Thr Val Pro Ala His Asp Ala Val Ile Ser Ser
530                 535                 540 gca gga acg cac tct gtt gct atg gtt act gct gag ggt aca gaa ggg      1798
Ala Gly Thr His Ser Val Ala Met Val Thr Ala Glu Gly Thr Glu Gly
545                 550                 555                 560 gaa cag gtt gca att gta gct caa gac ttg gca gca ttc cat act gcc      1846
Glu Gln Val Ala Ile Val Ala Gln Asp Leu Ala Ala Phe His Thr Ala
                565                 570                 575 tca tca gaa atg ggg cac cag cag cat agc cat cac tta gta acc aca      1894
Ser Ser Glu Met Gly His Gln Gln His Ser His His Leu Val Thr Thr
            580                 585                 590 gaa acc aga cct ctg acc tta gta gca aca tcc aat ggc acc cag att      1942
Glu Thr Arg Pro Leu Thr Leu Val Ala Thr Ser Asn Gly Thr Gln Ile
        595                 600                 605 gca gtt cag ctt gga gaa cag cca tct ctg gaa gaa gcc atc aga ata      1990
Ala Val Gln Leu Gly Glu Gln Pro Ser Leu Glu Glu Ala Ile Arg Ile
610                 615                 620 gcg tct aga atc caa caa gga gaa acg cca ggg ttg gat gat taa          2035
Ala Ser Arg Ile Gln Gln Gly Glu Thr Pro Gly Leu Asp Asp
625                 630                 635 tcctcagaac aatggagcaa taaagcagaa ggagtctttc atcttctggc agcagaaatc   2095
catgaagccc gggcccagga aaattagaag ttttccattc ctgatacact gtacacattt   2155
ttatgcgaga gtggagaaca ttttattctt gacacttttg tgtatataac ccttggaata   2215
gattctcaga gtgattcatt gtgtacaagg aagtatgaaa ttagggcaat acagtaaatt   2275
ttcatgttac tcttttatca gatcacaaac tcctagagtc tacatgcaag actagtaaag   2335
tcttatggag tcttatgatg gattttttaac ttcccgtgga aaaaaaaata aaggctgtat   2395
ctaaaatatc aaaggttcta tatgtcacac aatcgtaatt ccaaaagcca ttatggataa   2455
taaagggtgt aaagccttca gatatttccc cagttagtag agtgtctgcg gttttttgttc  2515 tactatatgc ttgtccattt ttatttgtat ctcatggttt gcagactgtt tgaataattt   2575
atagtttccc atccctgtta aaaaccagct cttcaagctg aaatgctaat tatattggca   2635
ttacattgaa ttatgtacaa aattataaaa tttggttatt taaaattaaa aagttaaatc   2695
cagtggtttt gttaaagatt ttgcttagta ttcaatttt attactgttt tttaaaaata    2755
atgaatcatc aaagttttaac cacaggctgg tgcccgggat aacagtactg taattggaaa  2815
```

```
tggctttact ctgaaaatta ggttagtggg ttggtgtaaa ttatttattt ttgcttatgt    2875 actttttgttt taaagcttat ttaccccaaa gtttattatt aattttgaat acagcaattt    2935
ttaaaatgtt a                                                          2946
```

<210> SEQ ID NO 7
<211> LENGTH: 638
<212> TYPE: PRT
<213> ORGANISM: Homo sapiens

<400> SEQUENCE: 7

```
Met Leu Leu Ala Gln Ile Asn Arg Asp Ser Gln Gly Met Thr Glu Phe
1               5                   10                  15

Pro Gly Gly Met Glu Ala Gln His Val Thr Leu Cys Leu Thr Glu
                20                  25                  30

Ala Val Thr Val Ala Asp Gly Asp Asn Leu Glu Asn Met Glu Gly Val
                35                  40                  45

Ser Leu Gln Ala Val Thr Leu Ala Asp Gly Ser Thr Ala Tyr Ile Gln
    50                  55                  60

His Asn Ser Lys Asp Ala Lys Leu Ile Asp Gly Gln Val Ile Gln Leu
65                  70                  75                  80

Glu Asp Gly Ser Ala Ala Tyr Val Gln His Val Pro Ile Pro Lys Ser
                85                  90                  95

Thr Gly Asp Ser Leu Arg Leu Glu Asp Gly Gln Ala Val Gln Leu Glu
            100                 105                 110

Asp Gly Thr Thr Ala Phe Ile His His Thr Ser Lys Asp Ser Tyr Asp
        115                 120                 125

Gln Ser Ala Leu Gln Ala Val Gln Leu Glu Asp Gly Thr Thr Ala Tyr
    130                 135                 140

Ile His His Ala Val Gln Val Pro Gln Ser Asp Thr Ile Leu Ala Ile
145                 150                 155                 160

Gln Ala Asp Gly Thr Val Ala Gly Leu His Thr Gly Asp Ala Thr Ile
                165                 170                 175

Asp Pro Asp Thr Ile Ser Ala Leu Glu Gln Tyr Ala Ala Lys Val Ser
            180                 185                 190

Ile Asp Gly Ser Glu Ser Val Ala Gly Thr Gly Met Ile Gly Glu Asn
        195                 200                 205

Glu Gln Glu Lys Lys Met Gln Ile Val Leu Gln Gly His Ala Thr Arg
    210                 215                 220

Val Thr Ala Lys Ser Gln Gln Ser Gly Glu Lys Ala Phe Arg Cys Glu
225                 230                 235                 240

Tyr Asp Gly Cys Gly Lys Leu Tyr Thr Thr Ala His His Leu Lys Val
                245                 250                 255

His Glu Arg Ser His Thr Gly Asp Arg Pro Tyr Gln Cys Glu His Ala
            260                 265                 270

Gly Cys Gly Lys Ala Phe Ala Thr Gly Tyr Gly Leu Lys Ser His Val
        275                 280                 285

Arg Thr His Thr Gly Glu Lys Pro Tyr Arg Cys Ser Glu Asp Asn Cys
    290                 295                 300

Thr Lys Ser Phe Lys Thr Ser Gly Asp Leu Gln Lys His Ile Arg Thr
305                 310                 315                 320

His Thr Gly Glu Arg Pro Phe Lys Cys Pro Phe Glu Gly Cys Gly Arg
                325                 330                 335

Ser Phe Thr Thr Ser Asn Ile Arg Lys Val His Val Arg Thr His Thr
            340                 345                 350
```

```
Gly Glu Arg Pro Tyr Tyr Cys Thr Glu Pro Gly Cys Gly Arg Ala Phe
            355                 360                 365

Ala Ser Ala Thr Asn Tyr Lys Asn His Val Arg Ile His Thr Gly Glu
        370                 375                 380

Lys Pro Tyr Val Cys Thr Val Pro Gly Cys Asp Lys Arg Phe Thr Glu
385                 390                 395                 400

Tyr Ser Ser Leu Tyr Lys His His Val Val His Thr His Ser Lys Pro
                405                 410                 415

Tyr Asn Cys Asn His Cys Gly Lys Thr Tyr Lys Gln Ile Ser Thr Leu
            420                 425                 430

Ala Met His Lys Arg Thr Ala His Asn Asp Thr Glu Pro Ile Glu Glu
        435                 440                 445

Glu Gln Glu Ala Phe Phe Glu Pro Pro Gly Gln Gly Glu Asp Val
450                 455                 460

Leu Lys Gly Ser Gln Ile Thr Tyr Val Thr Gly Val Glu Gly Asp Asp
465                 470                 475                 480

Val Val Ser Thr Gln Val Ala Thr Val Thr Gln Ser Gly Leu Ser Gln
                485                 490                 495

Gln Val Thr Leu Ile Ser Gln Asp Gly Thr Gln His Val Asn Ile Ser
            500                 505                 510

Gln Ala Asp Met Gln Ala Ile Gly Asn Thr Ile Thr Met Val Thr Gln
        515                 520                 525

Asp Gly Thr Pro Ile Thr Val Pro Ala His Asp Ala Val Ile Ser Ser
530                 535                 540

Ala Gly Thr His Ser Val Ala Met Val Thr Ala Glu Gly Thr Glu Gly
545                 550                 555                 560

Glu Gln Val Ala Ile Val Ala Gln Asp Leu Ala Ala Phe His Thr Ala
                565                 570                 575

Ser Ser Glu Met Gly His Gln His Ser His His Leu Val Thr Thr
            580                 585                 590

Glu Thr Arg Pro Leu Thr Leu Val Ala Thr Ser Asn Gly Thr Gln Ile
        595                 600                 605

Ala Val Gln Leu Gly Glu Gln Pro Ser Leu Glu Glu Ala Ile Arg Ile
610                 615                 620

Ala Ser Arg Ile Gln Gln Gly Glu Thr Pro Gly Leu Asp Asp
625                 630                 635

<210> SEQ ID NO 8
<211> LENGTH: 3013
<212> TYPE: DNA
<213> ORGANISM: Mus musculus
<220> FEATURE:
<221> NAME/KEY: CDS
<222> LOCATION: (82)..(1995)

<400> SEQUENCE: 8
gggggccggg cggctgtttc ctgtcctggt gcatggtggt cggacgaagg aattgttgga       60 aaatttctc ggaggtagaa a atg ttg tta gca caa ata aat cgg gat tct          111
                       Met Leu Leu Ala Gln Ile Asn Arg Asp Ser
                         1               5                  10 cag gga atg aca gaa ttt cct gga gga gga atg gag gct caa cat gtt        159
Gln Gly Met Thr Glu Phe Pro Gly Gly Gly Met Glu Ala Gln His Val
                15                  20                  25 acc ctg tgc ctg acg gag gca gta acc gtg gca gat ggt gac aat tta       207
Thr Leu Cys Leu Thr Glu Ala Val Thr Val Ala Asp Gly Asp Asn Leu
            30                  35                  40 gaa aat atg gaa ggt gtg agt tta caa gct gtg aca ctc gca gac ggc       255
```

```
                Glu Asn Met Glu Gly Val Ser Leu Gln Ala Val Thr Leu Ala Asp Gly
                        45                  50                  55 tct act gct tac ata cag cat aat tct aaa gac ggg aga ctc att gat         303
Ser Thr Ala Tyr Ile Gln His Asn Ser Lys Asp Gly Arg Leu Ile Asp
 60                  65                  70 ggc cag gtc att cag ctg gaa gat ggt tct gct gcc tat gtt cag cat         351
Gly Gln Val Ile Gln Leu Glu Asp Gly Ser Ala Ala Tyr Val Gln His
 75                  80                  85                  90 gtc ccc ata cct aaa agt agg gac agt ttg cgg ctg gag gat ggg caa         399
Val Pro Ile Pro Lys Ser Arg Asp Ser Leu Arg Leu Glu Asp Gly Gln
                 95                 100                 105 gca gtg cag cta gaa gac ggg acc act gca ttt atc cac cac acc tcg         447
Ala Val Gln Leu Glu Asp Gly Thr Thr Ala Phe Ile His His Thr Ser
            110                 115                 120 aaa gac agt tat gac cag agc tca ctt cag gcc gtt cag tta gaa gat         495
Lys Asp Ser Tyr Asp Gln Ser Ser Leu Gln Ala Val Gln Leu Glu Asp
        125                 130                 135 ggg aca aca gct tat atc cac cat gca gtg caa gtc cca cag tct gat         543
Gly Thr Thr Ala Tyr Ile His His Ala Val Gln Val Pro Gln Ser Asp
    140                 145                 150 acc atc ttg gca att cag gct gat ggg aca gtg gca ggg ctg cac act         591
Thr Ile Leu Ala Ile Gln Ala Asp Gly Thr Val Ala Gly Leu His Thr
155                 160                 165                 170 ggg gat gcc aca att gac cca gat acc att agt gct ttg gag cag tac         639
Gly Asp Ala Thr Ile Asp Pro Asp Thr Ile Ser Ala Leu Glu Gln Tyr
                175                 180                 185 gca gca aag gta tcc att gat ggc agt gac ggt gta aca agt aca gga         687
Ala Ala Lys Val Ser Ile Asp Gly Ser Asp Gly Val Thr Ser Thr Gly
            190                 195                 200 atg att gga gag aat gag caa gag aaa aaa atg cag att gtc tta caa         735
Met Ile Gly Glu Asn Glu Gln Glu Lys Lys Met Gln Ile Val Leu Gln
        205                 210                 215 ggc cat gct act cgg gta act cct aaa tct cag cag agt gga gaa aag         783
Gly His Ala Thr Arg Val Thr Pro Lys Ser Gln Gln Ser Gly Glu Lys
    220                 225                 230 gca ttt cgg tgc aaa tac gac ggc tgt ggg aaa ctc tat aca aca gct         831
Ala Phe Arg Cys Lys Tyr Asp Gly Cys Gly Lys Leu Tyr Thr Thr Ala
235                 240                 245                 250 cat cac ctt aag gtc cat gag cgc tca cac aca gga gac cgg cct tac         879
His His Leu Lys Val His Glu Arg Ser His Thr Gly Asp Arg Pro Tyr
                255                 260                 265 cag tgt gag cat tca ggc tgt ggg aaa gca ttt gca aca ggt tat gga         927
Gln Cys Glu His Ser Gly Cys Gly Lys Ala Phe Ala Thr Gly Tyr Gly
            270                 275                 280 tta aaa agt cat ttc aga act cat act gga gaa aag cca tat cgg tgt         975
Leu Lys Ser His Phe Arg Thr His Thr Gly Glu Lys Pro Tyr Arg Cys
        285                 290                 295 tca gaa gat aat tgt aca aag tct ttc aaa act tca gga gat cta cag        1023
Ser Glu Asp Asn Cys Thr Lys Ser Phe Lys Thr Ser Gly Asp Leu Gln
300                 305                 310 aag cac atc aga acc cat aca gga gaa agg ccc ttt aag tgt cct att        1071
Lys His Ile Arg Thr His Thr Gly Glu Arg Pro Phe Lys Cys Pro Ile
315                 320                 325                 330 gaa ggc tgt ggt cgg tcc ttt acc aca tca aat atc aga aaa gtg cac        1119
Glu Gly Cys Gly Arg Ser Phe Thr Thr Ser Asn Ile Arg Lys Val His
                335                 340                 345 att agg aca cac aca gga gaa aga cct tat tac tgc aca gaa cct gga        1167
Ile Arg Thr His Thr Gly Glu Arg Pro Tyr Tyr Cys Thr Glu Pro Gly
            350                 355                 360 tgt ggg agg gca ttt gcc agc gca act aat tat aaa aac cat gtg agg        1215
```

```
              Cys Gly Arg Ala Phe Ala Ser Ala Thr Asn Tyr Lys Asn His Val Arg
                              365                 370                 375 ata cac aca gga gaa aag cca tat gtc tgt aca gtt cct ggg tgt gac       1263
Ile His Thr Gly Glu Lys Pro Tyr Val Cys Thr Val Pro Gly Cys Asp
            380                 385                 390 aaa cgg ttt aca gaa tat tcc agt ttg tat aaa cac cat gtc gtt cac       1311
Lys Arg Phe Thr Glu Tyr Ser Ser Leu Tyr Lys His His Val Val His
395                 400                 405                 410 act cac tct aaa cca tac aac tgt aac cac tgt ggg aag acg tac aaa       1359
Thr His Ser Lys Pro Tyr Asn Cys Asn His Cys Gly Lys Thr Tyr Lys
                415                 420                 425 cag att tcc aca ctg gcc atg cac aaa cgg aca gcc cac aac gac aca       1407
Gln Ile Ser Thr Leu Ala Met His Lys Arg Thr Ala His Asn Asp Thr
            430                 435                 440 gag ccc att gag gag gag cag gaa gcc ttc ttc gag cct ccc cca ggt       1455
Glu Pro Ile Glu Glu Glu Gln Glu Ala Phe Phe Glu Pro Pro Pro Gly
                445                 450                 455 caa ggt gat gat gtt ctt aaa ggg tcc cag atc aca tat gtt aca ggt       1503
Gln Gly Asp Asp Val Leu Lys Gly Ser Gln Ile Thr Tyr Val Thr Gly
            460                 465                 470 gta gat gga gag gac att gta tct aca caa gta gcc aca gta acc cag       1551
Val Asp Gly Glu Asp Ile Val Ser Thr Gln Val Ala Thr Val Thr Gln
475                 480                 485                 490 tct ggg ctg agt caa caa gtc aca ctc ata tca cag gat ggg act caa       1599
Ser Gly Leu Ser Gln Gln Val Thr Leu Ile Ser Gln Asp Gly Thr Gln
                495                 500                 505 cat gtc aac ata tct caa gct gac atg cag gcc att ggc aac acc atc       1647
His Val Asn Ile Ser Gln Ala Asp Met Gln Ala Ile Gly Asn Thr Ile
            510                 515                 520 acc atg gta aca cag gat ggc aca ccc atc acg gtc ccc act cac gat       1695
Thr Met Val Thr Gln Asp Gly Thr Pro Ile Thr Val Pro Thr His Asp
                525                 530                 535 gca gtc atc tcc tca gca gga aca cat tct gtt gct atg gtt acc gcg       1743
Ala Val Ile Ser Ser Ala Gly Thr His Ser Val Ala Met Val Thr Ala
            540                 545                 550 gag ggc aca gaa gga cag cag gtc gca att gta gct caa gat ctg gca       1791
Glu Gly Thr Glu Gly Gln Gln Val Ala Ile Val Ala Gln Asp Leu Ala
555                 560                 565                 570 gcg ttc cat aca gca tct tca gag atg gga cac caa caa cat agc cat       1839
Ala Phe His Thr Ala Ser Ser Glu Met Gly His Gln Gln His Ser His
                575                 580                 585 cac cta gta act aca gaa acc aga cct ctg acc tta gtg gca aca tcc       1887
His Leu Val Thr Thr Glu Thr Arg Pro Leu Thr Leu Val Ala Thr Ser
            590                 595                 600 aac ggc acc cag atc gca gtt cag ctt gga gag cag ccg tct ctg gaa       1935
Asn Gly Thr Gln Ile Ala Val Gln Leu Gly Glu Gln Pro Ser Leu Glu
                605                 610                 615 gaa gct atc aga ata gca tcg agg atc caa caa ggg gag acg cca ggg       1983
Glu Ala Ile Arg Ile Ala Ser Arg Ile Gln Gln Gly Glu Thr Pro Gly
            620                 625                 630 ttg gat gat taa cactcggaat tacagagcaa taaaacagga ggaggagcct          2035
Leu Asp Asp
635 ttcatctctg gcggcagaat ccctgaagcc ctgcccggca gagcagaagt tccattcctg    2095 aagcactgga cacattttta tgcaagagta gagaacattt tcttcttgac acttttgtgt    2155 acatagcccc ggaatgaaat cccaacgtga ttcattgtgt acgaggaaga atgaaatgag    2215 ggctctgcag cagttcttca tgctactctt gaccacatgg caaattcctg aaatccaccc    2275 ataagatcag cagggtctga acacagtcaa gatgcgcttt taacttactg tgaaaaacac    2335
```

```
ggctgtatct aatgtgctga aggttctaca tgtgaaacaa tcataactcc aaagccatca    2395
cagaataaag gatgcaagcc ttcagctgtc cctccagtta atgtctggat tgtttgtcct    2455
aatacacacc catgtttact tggatttcaa ggtttgaaga cctcatttat agagcoccat    2515 ccctgttata taacacttct tcaagctaaa atgctgatta ttttagcatt acattggatt    2575
atgtataaaa ttacaaagtt tggttatttt aaattaaaac attaaatcca gtgtttgaag    2635
ctgggaatgg cagcttgtgc ctgtaatccc agcattaaag tcctgatgca ggaggagaac    2695
ataaatgtga gactaacctg ggctgtgtag tgaattccag gctaatctga gctactctca    2755
aaaaacaaga tatatccatt atttggggttg ttaaaatcag cctttttgatt ttttgctact    2815 gttttttatg ataatcaact atgagagttt cccacgggtc tggcctaggc ttatagttct    2875
atggctgaga atgaatttac tccaaaaaac tgggttagtg agttgtgtaa attatttatt    2935
tttgctccta atcttttgtt ttaaagctta tttaccttaa agtttattat tgactttgaa    2995
tacagcagtt tttaaaac                                                  3013
```

<210> SEQ ID NO 9
<211> LENGTH: 637
<212> TYPE: PRT
<213> ORGANISM: Mus musculus

<400> SEQUENCE: 9

```
Met Leu Leu Ala Gln Ile Asn Arg Asp Ser Gln Gly Met Thr Glu Phe
1               5                   10                  15

Pro Gly Gly Gly Met Glu Ala Gln His Val Thr Leu Cys Leu Thr Glu
            20                  25                  30

Ala Val Thr Val Ala Asp Gly Asp Asn Leu Glu Asn Met Glu Gly Val
        35                  40                  45

Ser Leu Gln Ala Val Thr Leu Ala Asp Gly Ser Thr Ala Tyr Ile Gln
    50                  55                  60

His Asn Ser Lys Asp Gly Arg Leu Ile Asp Gly Gln Val Ile Gln Leu
65                  70                  75                  80

Glu Asp Gly Ser Ala Ala Tyr Val Gln His Val Pro Ile Pro Lys Ser
                85                  90                  95

Arg Asp Ser Leu Arg Leu Glu Asp Gly Gln Ala Val Gln Leu Glu Asp
            100                 105                 110

Gly Thr Thr Ala Phe Ile His His Thr Ser Lys Asp Ser Tyr Asp Gln
        115                 120                 125

Ser Ser Leu Gln Ala Val Gln Leu Glu Asp Gly Thr Thr Ala Tyr Ile
    130                 135                 140

His His Ala Val Gln Val Pro Gln Ser Asp Thr Ile Leu Ala Ile Gln
145                 150                 155                 160

Ala Asp Gly Thr Val Ala Gly Leu His Thr Gly Asp Ala Thr Ile Asp
                165                 170                 175

Pro Asp Thr Ile Ser Ala Leu Glu Gln Tyr Ala Ala Lys Val Ser Ile
            180                 185                 190

Asp Gly Ser Asp Gly Val Thr Ser Thr Gly Met Ile Gly Glu Asn Glu
        195                 200                 205

Gln Glu Lys Lys Met Gln Ile Val Leu Gln Gly His Ala Thr Arg Val
    210                 215                 220

Thr Pro Lys Ser Gln Gln Ser Gly Glu Lys Ala Phe Arg Cys Lys Tyr
225                 230                 235                 240

Asp Gly Cys Gly Lys Leu Tyr Thr Thr Ala His His Leu Lys Val His
                245                 250                 255
```

Glu Arg Ser His Thr Gly Asp Arg Pro Tyr Gln Cys Glu His Ser Gly
            260                 265                 270

Cys Gly Lys Ala Phe Ala Thr Gly Tyr Gly Leu Lys Ser His Phe Arg
        275                 280                 285

Thr His Thr Gly Glu Lys Pro Tyr Arg Cys Ser Glu Asp Asn Cys Thr
    290                 295                 300

Lys Ser Phe Lys Thr Ser Gly Asp Leu Gln Lys His Ile Arg Thr His
305                 310                 315                 320

Thr Gly Glu Arg Pro Phe Lys Cys Pro Ile Glu Gly Cys Gly Arg Ser
                325                 330                 335

Phe Thr Thr Ser Asn Ile Arg Lys Val His Ile Arg Thr His Thr Gly
            340                 345                 350

Glu Arg Pro Tyr Tyr Cys Thr Glu Pro Gly Cys Gly Arg Ala Phe Ala
        355                 360                 365

Ser Ala Thr Asn Tyr Lys Asn His Val Arg Ile His Thr Gly Glu Lys
    370                 375                 380

Pro Tyr Val Cys Thr Val Pro Gly Cys Asp Lys Arg Phe Thr Glu Tyr
385                 390                 395                 400

Ser Ser Leu Tyr Lys His His Val Val His Thr His Ser Lys Pro Tyr
                405                 410                 415

Asn Cys Asn His Cys Gly Lys Thr Tyr Lys Gln Ile Ser Thr Leu Ala
            420                 425                 430

Met His Lys Arg Thr Ala His Asn Asp Thr Glu Pro Ile Glu Glu Glu
        435                 440                 445

Gln Glu Ala Phe Phe Glu Pro Pro Gly Gln Gly Asp Asp Val Leu
    450                 455                 460

Lys Gly Ser Gln Ile Thr Tyr Val Thr Gly Val Asp Gly Glu Asp Ile
465                 470                 475                 480

Val Ser Thr Gln Val Ala Thr Val Thr Gln Ser Gly Leu Ser Gln Gln
                485                 490                 495

Val Thr Leu Ile Ser Gln Asp Gly Thr Gln His Val Asn Ile Ser Gln
            500                 505                 510

Ala Asp Met Gln Ala Ile Gly Asn Thr Ile Thr Met Val Thr Gln Asp
        515                 520                 525

Gly Thr Pro Ile Thr Val Pro Thr His Asp Ala Val Ile Ser Ser Ala
    530                 535                 540

Gly Thr His Ser Val Ala Met Val Thr Ala Glu Gly Thr Glu Gly Gln
545                 550                 555                 560

Gln Val Ala Ile Val Ala Gln Asp Leu Ala Ala Phe His Thr Ala Ser
                565                 570                 575

Ser Glu Met Gly His Gln His Ser His His Leu Val Thr Thr Glu
            580                 585                 590

Thr Arg Pro Leu Thr Leu Val Ala Thr Ser Asn Gly Thr Gln Ile Ala
        595                 600                 605

Val Gln Leu Gly Glu Gln Pro Ser Leu Glu Glu Ala Ile Arg Ile Ala
    610                 615                 620

Ser Arg Ile Gln Gln Gly Glu Thr Pro Gly Leu Asp Asp
625                 630                 635

```
<210> SEQ ID NO 10
<211> LENGTH: 25
<212> TYPE: DNA
<213> ORGANISM: Homo sapiens

<400> SEQUENCE: 10
```

-continued

```
cctcggcttc ccaaaatgct gggat                                              25

<210> SEQ ID NO 11
<211> LENGTH: 25
<212> TYPE: DNA
<213> ORGANISM: Homo sapiens

<400> SEQUENCE: 11
aatacagctc ccaggttacc tcggg                                              25

<210> SEQ ID NO 12
<211> LENGTH: 25
<212> TYPE: DNA
<213> ORGANISM: Homo sapiens

<400> SEQUENCE: 12
acttcatttc ccaggagcct ccgcg                                              25

<210> SEQ ID NO 13
<211> LENGTH: 25
<212> TYPE: DNA
<213> ORGANISM: Homo sapiens

<400> SEQUENCE: 13
cattgctttc ccatcctgct actca                                              25

<210> SEQ ID NO 14
<211> LENGTH: 25
<212> TYPE: DNA
<213> ORGANISM: Homo sapiens

<400> SEQUENCE: 14
ggtggaattc ccatcttgca gccga                                              25

<210> SEQ ID NO 15
<211> LENGTH: 25
<212> TYPE: DNA
<213> ORGANISM: Homo sapiens

<400> SEQUENCE: 15
caggcactgc ccagcgtggc gagcc                                              25

<210> SEQ ID NO 16
<211> LENGTH: 25
<212> TYPE: DNA
<213> ORGANISM: Homo sapiens

<400> SEQUENCE: 16
actacgcctc ccagcgtgct ttgcg                                              25

<210> SEQ ID NO 17
<211> LENGTH: 25
<212> TYPE: DNA
<213> ORGANISM: Homo sapiens

<400> SEQUENCE: 17
tgcgcctctc ccttcagccc cggcc                                              25

<210> SEQ ID NO 18
<211> LENGTH: 25
<212> TYPE: DNA
<213> ORGANISM: Homo sapiens

<400> SEQUENCE: 18
```

```
cccttccctc ccccgtgct ctgcc                                          25

<210> SEQ ID NO 19
<211> LENGTH: 25
<212> TYPE: DNA
<213> ORGANISM: Homo sapiens

<400> SEQUENCE: 19
actacaatac ccaggacgca cccag                                         25

<210> SEQ ID NO 20
<211> LENGTH: 25
<212> TYPE: DNA
<213> ORGANISM: Homo sapiens

<400> SEQUENCE: 20
tctcgacttc ccaaagtgct gggat                                         25

<210> SEQ ID NO 21
<211> LENGTH: 25
<212> TYPE: DNA
<213> ORGANISM: Homo sapiens

<400> SEQUENCE: 21
ccagcctagc ccactgtgca tgaag                                         25

<210> SEQ ID NO 22
<211> LENGTH: 25
<212> TYPE: DNA
<213> ORGANISM: Homo sapiens

<400> SEQUENCE: 22
ttaatctgtc ccttaatgca cttac                                         25

<210> SEQ ID NO 23
<211> LENGTH: 25
<212> TYPE: DNA
<213> ORGANISM: Homo sapiens

<400> SEQUENCE: 23
gacgtagttc ccataggccc tccac                                         25

<210> SEQ ID NO 24
<211> LENGTH: 25
<212> TYPE: DNA
<213> ORGANISM: Homo sapiens

<400> SEQUENCE: 24
actactactc ccggcaggcc ttgtg                                         25

<210> SEQ ID NO 25
<211> LENGTH: 25
<212> TYPE: DNA
<213> ORGANISM: Homo sapiens

<400> SEQUENCE: 25
cccgccctcc ccaccaaccc acccg                                         25

<210> SEQ ID NO 26
<211> LENGTH: 25
<212> TYPE: DNA
<213> ORGANISM: Homo sapiens

<400> SEQUENCE: 26
```

-continued cctcggcttc ccaaagtgct gggat                                    25

<210> SEQ ID NO 27
<211> LENGTH: 25
<212> TYPE: DNA
<213> ORGANISM: Homo sapiens

<400> SEQUENCE: 27
cagggcgctc ccatggtgcc gcgcg                                    25

<210> SEQ ID NO 28
<211> LENGTH: 25
<212> TYPE: DNA
<213> ORGANISM: Homo sapiens

<400> SEQUENCE: 28
actacgaatc ccagaatgcc ctgtt                                    25

<210> SEQ ID NO 29
<211> LENGTH: 25
<212> TYPE: DNA
<213> ORGANISM: Homo sapiens

<400> SEQUENCE: 29
cgggtccttc ccacctcgcc attgg                                    25

<210> SEQ ID NO 30
<211> LENGTH: 19
<212> TYPE: DNA
<213> ORGANISM: Homo sapiens

<400> SEQUENCE: 30
actcccagaa cgcaatgcc                                           19

<210> SEQ ID NO 31
<211> LENGTH: 19
<212> TYPE: DNA
<213> ORGANISM: Homo sapiens

<400> SEQUENCE: 31
gtacccaccc agcaccgcg                                           19

<210> SEQ ID NO 32
<211> LENGTH: 19
<212> TYPE: DNA
<213> ORGANISM: Homo sapiens

<400> SEQUENCE: 32
tttcccgggg acccctgcg                                           19

<210> SEQ ID NO 33
<211> LENGTH: 19
<212> TYPE: DNA
<213> ORGANISM: Homo sapiens

<400> SEQUENCE: 33
gtgcccattt tgcattggg                                           19

<210> SEQ ID NO 34
<211> LENGTH: 19
<212> TYPE: DNA
<213> ORGANISM: Homo sapiens

<400> SEQUENCE: 34 cctcccccg tgctctgcc                                         19

<210> SEQ ID NO 35
<211> LENGTH: 19
<212> TYPE: DNA
<213> ORGANISM: Homo sapiens

<400> SEQUENCE: 35
gctcccaggt ctccgcgcg                                        19

<210> SEQ ID NO 36
<211> LENGTH: 19
<212> TYPE: DNA
<213> ORGANISM: Homo sapiens

<400> SEQUENCE: 36
atccccaaaa tccaagcca                                        19

<210> SEQ ID NO 37
<211> LENGTH: 19
<212> TYPE: DNA
<213> ORGANISM: Homo sapiens

<400> SEQUENCE: 37
cttcccaccc ggccaggtc                                        19

<210> SEQ ID NO 38
<211> LENGTH: 19
<212> TYPE: DNA
<213> ORGANISM: Homo sapiens

<400> SEQUENCE: 38 accccagct tgcacggcc                                         19

<210> SEQ ID NO 39
<211> LENGTH: 19
<212> TYPE: DNA
<213> ORGANISM: Homo sapiens

<400> SEQUENCE: 39
tctccccacc tgcctcccg                                        19

<210> SEQ ID NO 40
<211> LENGTH: 19
<212> TYPE: DNA
<213> ORGANISM: Homo sapiens

<400> SEQUENCE: 40 gccccaccc tccactggg                                         19

<210> SEQ ID NO 41
<211> LENGTH: 19
<212> TYPE: DNA
<213> ORGANISM: Homo sapiens

<400> SEQUENCE: 41
ttacccgccg cgctgcgcg                                        19

<210> SEQ ID NO 42
<211> LENGTH: 19
<212> TYPE: DNA
<213> ORGANISM: Homo sapiens

<400> SEQUENCE: 42

```
actcccagcg tgccgcgcg                                                   19

<210> SEQ ID NO 43
<211> LENGTH: 19
<212> TYPE: DNA
<213> ORGANISM: Homo sapiens

<400> SEQUENCE: 43
gctcccatgg tgccgcgcg                                                   19

<210> SEQ ID NO 44
<211> LENGTH: 19
<212> TYPE: DNA
<213> ORGANISM: Homo sapiens

<400> SEQUENCE: 44
actcccagga tgcccttcc                                                   19
```

METHOD OF INHIBITING CANCER CELL PROLIFERATION, PROLIFERATION INHIBITOR AND SCREENING METHOD

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 38,549 bytes ASCII (Text) file named "706579SequenceListing.txt," created Jun. 24, 2010.

TECHNICAL FIELD

The present invention relates to a method of inhibiting cancer cell proliferation, comprising suppressing a function of the gene that encodes Zinc finger protein 143 (hereinafter, also referred to as ZNF143), which is the human homologue of the clawed frog (Xenopus) transcriptional activator, which is associated with the selenocysteine tRNA gene, a cancer cell proliferation inhibitor comprising as an active ingredient a substance capable of inhibiting a function of ZNF143, like a ZNF143-specific siRNA, a screening method for a substance possessing cancer cell proliferation inhibitory activity with the amount of inhibition of binding of the ZNF143 protein as an index, and the like.

BACKGROUND ART

Cancer is a fatal disease accounting for a large percentage of the causes of death in humans. Currently, the ratio of cancer to the causes of death is still tending to rise. Available methods of its treatment include surgical therapy, radiotherapy, chemotherapy and the like. In addition to these therapies, there have been developed inhibitors that target molecules that are highly expressed specifically in cancer cells and promote cell proliferation, and what is called molecular targeted therapy is implemented. However, search for new molecular targets and ensuing drug discovery still represents the most important research objects.

The present inventors searched for genes whose expression is induced by DNA damage signals by the differential display method. As a result, the present inventors identified the transcription factor ZNF143. This gene was isolated and identified as a transcription factor of the selenocysteine tRNA gene from the African clawed frog in 1995 (Non-patent document 1). Later, a functional analysis thereof as a transcription factor was announced. The present inventors reported that the expression of ZNF143 is induced at the transcriptional level by anticancer agents and gamma rays, which cause DNA damage, and that ZNF143 recognizes cisplatin-bridged DNA (Non-patent document 2). Furthermore, the present inventors found that ZNF143 is highly expressed in cisplatin-resistant cancer cells, that the cells become sensitive to cisplatin when the expression of ZNF143 is suppressed, and that ZNF143 positively controls the expression of many DNA repair gene groups (Non-patent document 3).

Results of a genome-wide search for sequences that bind to the ZNF143 polypeptide have been reported so far (Non-patent document 4). The report concerns analytical results for genome information and represents nothing more than the finding of a broad range of different genes associated with ZNF143. The report does not analyze what functions are possessed by the broad range of genes at all.

Meanwhile, mechanisms for cancer cell proliferation are being elucidated at the molecular level. In particular, molecules that influence the cell cycle are attracting attention as preferred molecular targets for cancer treatment.

Regarding the cell cycle, a brief explanation is given here. The cell cycle consists of four processes; the individual processes are called the G1 phase, S phase (DNA replication phase), G2 phase, and M phase (division phase), arranged in time sequence. At the ends of the G1 phase and G2 phase (the latter also referred to as the G2/M phase), a surveillance mechanism for sensing DNA abnormalities works, and this mechanism is called a checkpoint. If a DNA abnormality is repairable by a DNA repair mechanism, the cell cycle proceeds as the DNA abnormality is repaired. If the DNA abnormality is unrepairable, cell death is induced, disenabling the survival of the abnormal cells.

In normal cells, DNA replication proceeds accurately, so it is thought that abnormalities are sensed by making use of the G1 phase checkpoint before the S phase, while the G2 phase checkpoint is hardly utilized. Meanwhile, in the majority of cancer cells, the G1 phase checkpoint is disordered and fails to function, and the G2 phase checkpoint is in an activated state instead. Therefore, to prevent DNA abnormalities from being repaired to cause cell death by inhibiting the G2 phase checkpoint in cancer cells is the most purposeful for a therapeutic drug for cancer. Furthermore, such therapeutic drugs seem to have less influence on normal cells.

Non-patent document 1: Schuster C. et al. EMBO J. 1995, 14, p3777-3787

Non-patent document 2: Ishiguchi H. et al. Int. J. Cancer 2004, 111, p900-909

Non-patent document 3: Wakasugi T. et al. Oncogene 2007 26, p5194-5203

Non-patent document 4: Myslinski E. et al. J. Biol Chem 2006 281, p39953-39963

DISCLOSURE OF THE INVENTION

Problems to be Solved by the Invention

It is an object of the present invention to provide an effective, reliable method of inhibiting cancer cell proliferation, a cancer cell proliferation inhibitor that is effective in cancer treatment, a prophylactic and/or therapeutic drug for cancer, a method of detecting a cancer cell, a diagnostic reagent for cancer, a vector and transformant cell, and a screening method for a substance possessing cancer cell proliferation inhibitory activity.

Means for Solving the Problems

The present inventors searched for a gene whose expression is altered by expressional suppression using a ZNF143-specific siRNA by DNA microarray. As a result, the present inventors found that ZNF143 specifically controls a plurality of gene groups involved in DNA replication, repair, and cell division. The present inventors also found by nucleotide sequence analysis of the promoter regions of the aforementioned gene groups that the ZNF143-binding nucleotide sequence is present roughly within 1 Kbp upstream of the transcription initiation point. The present inventors also demonstrated that ZNF143 is surely capable of binding to the sequence. The present inventors also found by the chromatin immunoprecipitation method using cancer cells that express tagged ZNF143 that ZNF143 is also bound to these sequences in the cells.

Further proceeding to analyze the functions of ZNF143, the present inventors found that expressional suppression with ZNF143-specific siRNA suppresses cancer cell proliferation and causes the cell cycle to stop in the G2/M phase. These facts show that ZNF143 is profoundly associated with cell proliferation. Hence, the present inventors analyzed the expression of ZNF143 by immunohistological staining using a ZNF143-specific antibody (polyclonal antibody). As a result, specific expression of ZNF143 was observed in the nuclei of cancer cells in cancer tissues, which are representative of proliferative diseases, with almost no expression observed in the cells of surrounding normal tissues. The present invention has been developed on the basis of these findings.

Accordingly, the present invention relates to the following:

[1] A method of inhibiting cancer cell proliferation, comprising suppressing a function of ZNF143.

[2] The method described in [1], wherein the function is suppressed by using a polynucleotide comprising a nucleotide sequence complementary to a nucleotide sequence that encodes ZNF143 or a partial sequence thereof with 15 consecutive bases or more, or an expression vector capable of expressing the polynucleotide.

[3] The method described in [2], wherein the polynucleotide is a double-stranded RNA comprising a nucleotide sequence complementary to the nucleotide sequence shown by SEQ ID NO:6 or 8 or a partial sequence thereof with 21 consecutive bases or more.

[4] The method described in [2], wherein the polynucleotide is a double-stranded RNA comprising a polynucleotide comprising the nucleotide sequence shown by any of SEQ ID NO:1 to 3 or a partial sequence thereof with 21 to 24 consecutive bases, and a polynucleotide complementary to the polynucleotide.

[5] The method described in [1], wherein the function is suppressed by using a polynucleotide comprising any ZNF143-binding nucleotide sequence selected from among the following nucleotide sequences, or an expression vector capable of expressing the polynucleotide:
(1) the nucleotide sequence shown by SEQ ID NO:4; and
(2) a nucleotide sequence having an identity of 60% or more to the nucleotide sequence shown by SEQ ID NO:4, wherein the 4th, 5th, and 6th cytosines of the nucleotide sequence shown by SEQ ID NO:4 are conserved, and wherein the 13th nucleotide is cytosine or guanine.

[6] The method described in [1], wherein the cancer is any selected from the group consisting of colorectal cancer, lung cancer, ovarian cancer, breast cancer, gall bladder cancer. prostatic cancer and uterine cervical cancer.

[7] A cancer cell proliferation inhibitor containing a substance that suppresses a function of ZNF143.

[8] The agent described in [7], wherein the substance is a polynucleotide comprising a nucleotide sequence complementary to a nucleotide sequence that encodes ZNF143 or a partial sequence thereof with 15 consecutive bases or more, or an expression vector capable of expressing the polynucleotide.

[9] The agent described in [8], wherein the nucleotide is a double-stranded RNA comprising a nucleotide sequence complementary to the nucleotide sequence shown by SEQ ID NO:6 or 8 or a partial sequence thereof with 21 consecutive bases or more.

[10] The agent described in [8], wherein the nucleotide is a double-stranded RNA comprising a polynucleotide comprising the nucleotide sequence shown by any of SEQ ID NO:1 to 3 or a partial sequence thereof with 21 to 24 consecutive bases, and a polynucleotide complementary to the polynucleotide.

[11] The agent described in [7], wherein the substance is a polynucleotide comprising any ZNF143-binding nucleotide sequence selected from among the following nucleotide sequences, or an expression vector capable of expressing the polynucleotide:
(1) the nucleotide sequence shown by SEQ ID NO:4; and
(2) a nucleotide sequence having an identity of 60% or more to the nucleotide sequence shown by SEQ ID NO:4, wherein the 4th, 5th, and 6th cytosines of the nucleotide sequence shown by SEQ ID NO:4 are conserved, and wherein the 13th nucleotide is cytosine or guanine.

[12] The agent described in [7], wherein the cancer is any selected from the group consisting of colorectal cancer, lung cancer, ovarian cancer, breast cancer, gall bladder cancer, prostatic cancer and uterine cervical cancer.

[13] A prophylactic and/or therapeutic drug for a cancer, wherein the drug contains as an active ingredient a substance that suppresses a function of ZNF143.

[14] The prophylactic and/or therapeutic drug described in [13], wherein the substance is a polynucleotide comprising a nucleotide sequence complementary to a nucleotide sequence that encodes ZNF143 or a partial sequence thereof with 15 consecutive bases or more, or an expression vector capable of expressing the polynucleotide.

[15] The prophylactic and/or therapeutic drug described in [14], wherein the polynucleotide is a double-stranded RNA comprising a nucleotide sequence complementary to the nucleotide sequence shown by SEQ ID NO:6 or 8 or a partial sequence thereof with 21 consecutive bases or more.

[16] The prophylactic and/or therapeutic drug described in [14], wherein the polynucleotide is a double-stranded RNA comprising a polynucleotide comprising the nucleotide sequence shown by any of SEQ ID NO:1 to 3 or a partial sequence thereof with 21 to 24 consecutive bases, and a polynucleotide complementary to the polynucleotide.

[17] The prophylactic and/or therapeutic drug described in [13], wherein the substance is a polynucleotide comprising any ZNF143-binding nucleotide sequence selected from among the following nucleotide sequences, or an expression vector capable of expressing the polynucleotide:
(1) the nucleotide sequence shown by SEQ ID NO:4; and
(2) a nucleotide sequence having an identity of 60% or more to the nucleotide sequence shown by SEQ ID NO:4, wherein the 4th, 5th, and 6th cytosines of the nucleotide sequence shown by SEQ ID NO:4 are conserved, and wherein the 13th nucleotide is cytosine or guanine.

[18] The prophylactic and/or therapeutic drug described in [13], wherein the cancer is any selected from the group consisting of colorectal cancer, lung cancer, ovarian cancer, breast cancer, gall bladder cancer, prostatic cancer and uterine cervical cancer.

[19] A method of detecting a cancer cell in a tissue, comprising measuring the expression level of ZNF143 in the tissue, and determining whether or not a cancer cell is contained in the tissue on the basis of the expression level.

[20] A diagnostic reagent for cancer comprising a nucleic acid probe or primer capable of specifically detecting a polynucleotide that encodes ZNF143, or an antibody that specifically recognizes ZNF143.

[21] A vector having a nucleotide sequence wherein a nucleotide sequence that encodes a monitoring gene is functionally joined downstream of any ZNF143-binding nucleotide sequence selected from among the following nucleotide sequences:
(1) the nucleotide sequence shown by SEQ ID NO:4; and
(2) a nucleotide sequence having an identity of 60% or more to the nucleotide sequence shown by SEQ ID NO:4, wherein the 4th, 5th, and 6th cytosines of the nucleotide sequence shown by SEQ ID NO:4 are conserved, and wherein the 13th nucleotide is cytosine or guanine.

[22] A cell transformed with the vector described in [21].

[23] A screening method for a substance possessing cancer cell proliferation inhibitory activity, comprising selecting a substance capable of suppressing a function of ZNF143 as a substance capable of inhibiting cancer cell proliferation.

[24] The method described in [23], comprising the following steps of:
(a) culturing a cell transformed with a vector having a nucleotide sequence wherein a nucleotide sequence that encodes a monitoring gene is functionally joined downstream of a ZNF143-binding nucleotide sequence, in the presence of a test substance,
(b) measuring the expression amount of the monitoring gene in the cell cultured in the presence of the test substance, and comparing the expression amount with the expression amount in a control cell cultured in the absence of the test substance, and
(c) selecting a test substance that suppresses the expression amount of the monitoring gene as a substance capable of inhibiting cancer cell proliferation on the basis of the results of the comparison (b).

[25] The method described in [24], wherein the cell cultured in (a) is a cancer cell.

Effect of the Invention

According to the present invention, a method of inhibiting cancer cell proliferation, comprising inhibiting a function of ZNF143; an excellent cancer cell proliferation inhibitor (anticancer agent) of high specificity for cancer cells containing as an active ingredient a function-inhibiting substance such as a substance that suppresses the expression of ZNF143, like a ZNF143-specific siRNA, and the like are provided, and a screening method for a substance possessing cancer cell proliferation inhibitory activity is also provided.

BRIEF DESCRIPTION OF THE DRAWINGS

FIG. 1 is a list of genes under the positive control of ZNF143, identified in Example 1.

FIG. 2 shows immunohistologically stained images of clinical cancer samples (breast cancer, uterine cervical cancer) stained in Example 2.

Figure 3:
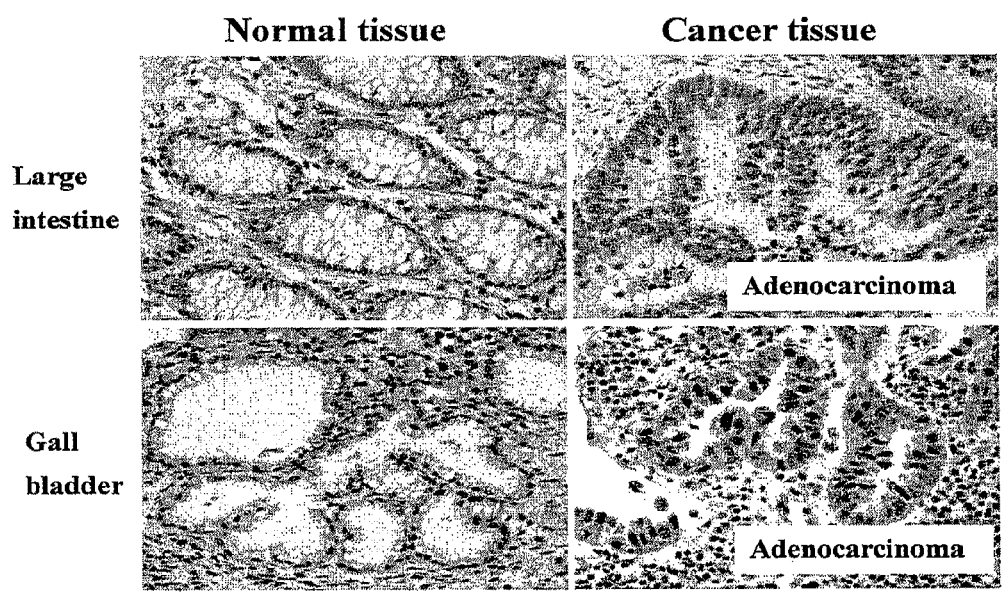
FIG. 3 shows immunohistologically stained images of clinical cancer samples (colorectal cancer, gall bladder cancer) stained in Example 2.

BEST MODE FOR CARRYING OUT THE INVENTION (1. Inhibition of Cancer Cell Proliferation by Suppression of Function of ZNF143)

The present invention provides an agent comprising a substance that suppresses a function of ZNF143. By administering the substance to a mammal to suppress a function of ZNF143, it is possible to inhibit cancer cell proliferation in the mammal to prevent or treat cancer. Therefore, the agent of the present invention is useful as a cancer cell proliferation inhibitor or as a prophylactic and/or therapeutic drug for cancer.

ZNF143 is a publicly known transcription factor that controls the expression of gene groups associated with DNA replication, repair, and cell division and the like. The ZNF143 that can be used in the present invention is of mammalian derivation. As examples of the mammal, laboratory animals such as rodents such as mice, rats, hamsters, and guinea pigs, and rabbits; domestic animals such as pigs, bovines, goat, horses, sheep and minks; companion animals such as dogs and cats; primates such as humans, monkeys, rhesuses, marmosets, orangutans, and chimpanzees; and the like can be mentioned. The mammal is preferably a rodent (for example, mouse) or a primate (for example, human). Amino acid sequences and nucleotide sequences of ZNF143 are also publicly known, and can be obtained from publicly known gene sequence databases (example: NCBI database). As an amino acid sequence of human ZNF143, the amino acid sequence shown by SEQ ID NO:7 (NCBI accession number: NP_003433) is known. As a nucleotide sequence (cDNA sequence) that encodes human ZNF143, the nucleotide sequence shown by SEQ ID NO:6 (NCBI accession number: NM_003442) is known. As an amino acid sequence of mouse ZNF143, the amino acid sequence shown by SEQ ID NO:9 (NCBI accession number: NP_033307) is known. As a nucleotide sequence (cDNA sequence) that encodes mouse ZNF143, the nucleotide sequence shown by SEQ ID NO:8 (NCBI accession number: NM_009281) is known.

When a nucleic acid having a certain nucleotide sequence is described herein, the term must be understood to be used with a meaning encompassing all single-stranded polynucleotides having the nucleotide sequence, single-stranded polynucleotides having a sequence complementary to the nucleotide sequence; and double-stranded polynucleotides which are hybrids thereof, unless otherwise stated.

A function of ZNF143 refers to a biological function (activity) possessed by the translation product (i.e., polypeptide) of the ZNF143 gene. As a function of ZNF143, binding to a ZNF143-binding nucleotide sequence (for example, the nucleotide sequence portion shown by SEQ ID NO:4) on a chromosome or expression vector to increase the expression of a gene functionally joined downstream thereof can be mentioned. As examples of preferable ZNF143-binding nucleotide sequences, the nucleotide sequences shown by any of SEQ ID NO:10 to 44 and the like can be mentioned.

Here, "functional joining" refers to a mode of joining such that a ZNF143-binding nucleotide sequence acts as a gene promoter in a cell to induce gene expression as a result of the binding of ZNF143 to the ZNF143-binding nucleotide sequence. Normally, the ZNF143-binding nucleotide sequence is placed in the 5' of the gene. The distance between the ZNF143-binding nucleotide sequence and the initiation codon of the gene is normally 20 to 150 bp, and is not particularly limited, as far as "functional joining" is achieved. The nucleotide sequence interposing between the ZNF143-binding nucleotide sequence and the transcription initiation point of the gene is also not particularly limited, as far as "functional joining" is achieved.

Herein, "suppressing the function of ZNF143" includes, in addition to direct inhibition of the above-described function exhibited by the ZNF143 polypeptide, suppressing the ZNF143 polypeptide from exhibiting its function as a result of suppression of the expression of the ZNF143 gene. Therefore, in the present invention, suppression of a function of ZNF143 can be performed at an optionally chosen level known to those skilled in the art, for example, the ZNF143 gene transcription level, the ZNF143 polypeptide production level, or the ZNF143 polypeptide activity expression level.

Suppression of the ZNF143 gene at the transcription level can be performed using a polynucleotide comprising a nucleotide sequence complementary to a nucleotide sequence that encodes ZNF143 or a partial sequence thereof with 15 consecutive bases or more, or a vector capable of expressing the polynucleotide. The nucleotide is capable of acting as a nucleotide that induces an RNA interference (RNAi) such as siRNA that targets the ZNF143 gene (DNA or mRNA) (a single-stranded RNA or double-stranded RNA having a partial nucleotide sequence of a nucleotide sequence complementary to a nucleotide sequence that encodes ZNF143, with 21 consecutive bases or more), antisense nucleotide, or various ribozymes and the like to suppress the expression of ZNF143.

Nucleotide sequences that encode ZNF143 include nucleotide sequences of cDNAs, mRNAs, initial transcription products (immature mRNAs), and chromosomal DNAs that encode ZNF143; more specifically, for example, nucleotide sequences of cDNA that encodes human ZNF143 (for example, SEQ ID NO:6), nucleotide sequences of cDNAs that encode mouse ZNF143 (for example, SEQ ID NO:8) and the like can be mentioned.

A polynucleotide having a nucleotide sequence complementary to the target region of a desired polynucleotide, i.e., a polynucleotide capable of hybridizing with a desired nucleotide under physiological conditions (for example, intracellular and the like), can be described as being "antisense" against the desired polynucleotide". Here, "complementary" refers to having a complementarity of about 70% or more, preferably about 80% or more, more preferably about 90% or more, still more preferably about 95% or more, most preferably 100%, between the nucleotide sequences. Nucleotide sequence identity as mentioned herein can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

A nucleotide comprising a nucleotide sequence complementary to a nucleotide sequence that encodes ZNF143 or a partial sequence thereof (hereinafter, also referred to as "an antisense ZNF143") can be designed and synthesized on the basis of information on a cloned or determined nucleotide sequence that encodes ZNF143. Such a polynucleotide is capable of inhibiting the replication or expression of the ZNF143 gene. Specifically, antisense ZNF143 is capable of hybridizing with an RNA (mRNA or initial transcription product) transcribed from a gene (chromosomal DNA) that encodes ZNF143 under physiological conditions (for example, intracellular and the like) to inhibit the synthesis (processing) or a function (translation into protein) of the mRNA.

The target region for an antisense ZNF143 is not particularly limited with respect to the length thereof, as far as the translation into the ZNF143 polypeptide is inhibited as a result of hybridization of an antisense nucleic acid; the target region may be the full-length sequence or a partial sequence of the mRNA or initial transcription product that encodes the polypeptide; the length is about 15 bases for the shortest, and the full-length sequence of the mRNA or initial transcription product for the longest. In view of the ease of synthesis, an oligonucleotide consisting of about 15 to about 30 bases is preferred, but the length is not limited to this range. From this viewpoint, an antisense ZNF143 used in the present invention comprises a nucleotide sequence complementary to a nucleotide sequence that encodes ZNF143 or a partial sequence thereof with 15 consecutive bases or more (preferably 18 bases or more, more preferably 21 bases or more).

Specifically, the 5' end hairpin loop, 5' end 6-base-pair repeat, 5' end noncoding region, translation initiation codon, protein coding region, translation stop codon, 3' end noncoding region, 3' end palindrome region, and 3' end hairpin loop of a nucleic acid (for example, mRNA or initial transcription product) that encodes ZNF143 may be chosen as a target region, but any other region in the polynucleotide that encodes ZNF143 can also be chosen as a target. For example, it is also preferable to use the intron portion of the ZNF143 gene as a target region.

Furthermore, the antisense ZNF143 may be not only capable of hybridizing with the mRNA or initial transcription product that encodes the ZNF143 polypeptide to inhibit its translation into the polypeptide, but also capable of binding to the double-stranded DNA that encodes the ZNF143 polypeptide to form a triple-strand (triplex) and inhibit the transcription of the RNA.

The choice of antisense polynucleotide may be a DNA or a RNA, or may be a DNA/RNA chimera. The antisense polynucleotide is single-stranded or double-stranded. A natural-type antisense polynucleotide has the phosphoric acid diester linkage thereof easily decomposed by nucleases present in cells, so an antisense polynucleotide can also be synthesized using a modified nucleotide such as the thiophosphate type (P=O in phosphate linkage replaced with P=S), 2'-O-methyl type, or morpholino-oligo group modified type, which are stable to the decomposing enzymes.

In the present invention, a ribozyme capable of specifically cleaving the mRNA or initial transcription product that encodes ZNF143 in the coding region (including the intron portion in the case of initial transcription product) can also be encompassed in the scope of antisense ZNF143. "A ribozyme" refers to an RNA possessing an enzyme activity to cleave nucleic acids; because it has recently been shown that an oligo-DNA having the nucleotide sequence of the enzyme activity site also possesses nucleic acid cleavage activity, this term is to be used herein as a concept encompassing a DNA, as far as the DNA possesses sequence-specific nucleic acid cleavage activity. The most versatile ribozyme is self-splicing RNA, found in infectious RNAs such as those of viroid and virosoid; this self-splicing RNA is known to occur in some types, including hammerhead type and hairpin type. The hammerhead type exhibits enzyme activity with about 40 bases in length, and it is possible to specifically cleave the target mRNA by making several bases at both ends adjoining to the hammerhead structure portion (about 10 bases in total) be a sequence complementary to the desired cleavage site of the mRNA. Furthermore, when ribozyme is used in the form of an expression vector comprising a DNA that encodes the same, a hybrid ribozyme wherein a sequence modified from tRNA is further linked to promote the localization of the transcription product to cytoplasm may be used [Nucleic Acids Res., 29(13): 2780-2788 (2001)].

A double-stranded RNA comprising a nucleotide sequence complementary to the nucleotide sequence of the mRNA or initial transcription product that encodes ZNF143 or a partial sequence thereof with 21 consecutive bases or more is a preferred antisense ZNF143. It had been known that so-called RNA interference (RNAi), which is a phenomenon that if a double-stranded RNA is introduced into cells, an mRNA complementary to one chain of the RNA is degraded, occurs in nematodes, insects, plants and the like; since this phenomenon was confirmed to also occur in mammalian cells [Nature, 411(6836): 494-498 (2001)], it has been widely utilized as an alternative technique to ribozymes.

The above-described double-stranded RNA is typically a double-stranded oligo-RNA consisting of an RNA having the nucleotide sequence of the mRNA or initial transcription product of ZNF143 or a partial sequence thereof (hereinafter, target nucleotide sequence) and a chain complementary thereto. A single-stranded RNA wherein a target nucleotide sequence (first sequence) and a sequence complementary thereto (second sequence) are joined via a hairpin loop moiety, with the first sequence forms a double-stranded structure with the second sequence by assuming a hairpin loop structure (small hairpin RNA: shRNA), is also included in the above-described double-stranded RNA.

The length of the portion complementary to the target nucleotide sequence, contained in the above-described double-stranded RNA, is normally about 21 bases or more, but is not particularly limited, as far as it can cause RNA interference. If the double-stranded RNA is longer than 23 bases, the double-stranded RNA can undergo degradation by Dicer in cells to produce an siRNA about 20 bases long (usually 21 to 23 bases); therefore, theoretically, the upper limit of the portion complementary to the target nucleotide sequence is the full length of the nucleotide sequence of the mRNA or initial transcription product of ZNF143. However, in view of the ease of synthesis, antigenicity issues and the like, the length of the complementary portion is, for example, about 200 bases or less, preferably about 50 bases or less, more preferably about 30 bases or less. Hence, the length of the complementary portion is, for example, about 21 bases or more, preferably about 21 to about 200 bases, more preferably about 21 to about 50 bases, still more preferably about 21 to about 30 bases, most preferably about 21 to about 27 bases.

The full length of the double-stranded RNA is normally about 21 bases or more, and is not particularly limited, as far as it can cause RNA interference; theoretically, there is no upper limit of the length of the double-stranded RNA. However, in view of the ease of synthesis, antigenicity issues and the like, the length of the double-stranded RNA is, for example, about 200 bases or less, preferably about 50 bases or less, more preferably about 30 bases or less. Hence, the length of the double-stranded RNA is, for example, about 21 bases or more, preferably about 21 to about 200 bases, more preferably about 21 to about 50 bases, still more preferably about 21 to about 30 bases, most preferably about 21 to about 27 bases. The length of the shRNA nucleic acid is expressed as the length of the double-stranded moiety when the shRNA assumes a double-stranded structure.

The double-stranded RNA may have at its 5' or 3' end an additional base consisting of 5 bases or less, preferably 2 bases, that does not form a base pair. Although the additional base may be DNA or RNA, the stability of the double-stranded RNA can be improved by using DNA. Examples of the sequence of such an additional base include, but are not limited to, sequences such as ug-3', uu-3', tg-3', tt-3', ggg-3', guuu-3', gttt-3', ttttt-3', and uuuuu-3'.

The length of the loop moiety of the hairpin loop of shRNA is not particularly limited, as far as it can cause RNI interference, and the length is normally about 5 to about 25 bases. The nucleotide sequence of the loop moiety is not particularly limited, as far as it can form a loop, and the shRNA can cause RNA interference.

In one preferred embodiment, a nucleotide used in the present invention is a double-stranded RNA comprising a nucleotide sequence complementary to the nucleotide sequence shown by SEQ ID NO:6 or 8 or a partial sequence thereof with about 21 consecutive bases or more. The double-stranded RNA comprises a polynucleotide (RNA) comprising a nucleotide sequence complementary to the nucleotide sequence shown by SEQ. ID NO:6 or 8 or a partial sequence thereof with about 21% consecutive bases or more and a polynucleotide (RNA) complementary to the polynucleotide, and the two RNAs can constitute the double-strand by hybridizing with each other.

Another preferred nucleotide used in the present invention is a double-stranded RNA comprising a polynucleotide (RNA) comprising the nucleotide sequence shown by any of SEQ ID NO:1 to 3 or a partial sequence thereof with about 21 to about 30 consecutive bases, and a polynucleotide (RNA) complementary to the polynucleotide. In the double-stranded RNA, the RNA comprising the nucleotide sequence shown by any of SEQ ID NO:1 to 3 or a partial sequence thereof with about 21 to about 30 consecutive bases and the RNA complementary to the polynucleotide can constitute the double-strand by hybridizing with each other.

An antisense ZNF143 can be prepared by determining the target sequence for the mRNA or initial transcription product on the basis of the cDNA sequence or genomic DNA sequence of ZNF143, and synthesizing a sequence complementary thereto using a commercially available automated DNA/RNA synthesizer (Applied Biosystems, Beckman and the like). A double-stranded RNA can be prepared by separately synthesizing a sense strand and an antisense strand using an automated DNA/RNA synthesizer, and denaturing the strands in an appropriate annealing buffer solution at about 90° C. to about 95° C. for about 1 minute, and then performing annealing at about 30° C. to about 70° C. for about 1 to about 8 hours.

In the present invention, an expression vector capable of expressing (that encodes) the above-described antisense ZNF143 may be used. In the expression vector, normally, a polynucleotide that encodes the above-described antisense ZNF143 is functionally joined to a promoter capable of exhibiting promoter activity in the cells of the mammal that is the subject of administration.

The promoter used is not particularly limited, as far as it is capable of functioning in the cells of the mammal that is the subject of administration. Useful promoters include poll-series promoters, polII-series promoters, polIII-series promoters and the like. Specifically, viral promoters such as the SV40-derived initial promoter and cytomegalovirus LTR, mammalian constitutive protein gene promoters such as the β-actin gene promoter, the tRNA promoter, and the like are used.

When the antisense ZNF143 encoded is an RNA, it is preferable to use a polIII-series promoter as the promoter. As examples of the polIII-series promoter, the U6 promoter, H1 promoter, tRNA promoter and the like can be mentioned.

The expression vector used in the present invention preferably contains a transcription termination signal, i.e., a terminator region, downstream of the antisense ZNF143. Furthermore, the expression vector may further contain a selection marker gene for transformant cell selection (a gene that confers resistance to a drug such as tetracycline, ampicillin, or kanamycin, a gene that compensates for auxotrophic mutations, and the like).

Although the choice of expression vector used in the present invention is not particularly limited, suitable vectors for administration to mammals such as humans include viral vectors such as retrovirus, adenovirus, and adeno-associated virus, as well as plasmid vectors. Adenovirus, in particular, has advantages such as very high gene transfer efficiency and transferability to non-dividing cells. Because the integration of transgenes into host chromosome is extremely rare, however, the gene expression is transient and normally persists only for about 4 weeks. In view of the persistence of therapeutic effect, it is also preferable to use adeno-associated virus, which offers a relatively high gene transfer efficiency, which can be transferred to non-dividing cells as well, and which can be integrated into chromosome via an inverted terminal repeat (ITR).

As suppression of the activity expression level of the ZNF143 polypeptide, inhibition of DNA binding or transcriptional function of the ZNF143 polypeptide can be mentioned. As stated above, ZNF143 has the function of binding to a ZNF143-binding nucleotide sequence (for example, the nucleotide sequence portion shown by SEQ ID NO:4) site on a chromosome or expression vector under physiological conditions (for example, intracellular and the like) to increase the expression of a gene functionally joined downstream thereof. Therefore, by administering a polynucleotide (decoy polynucleotide) comprising a ZNF143-binding nucleotide sequence (for example, any nucleotide sequence selected from among the nucleotide sequences shown below) or an expression vector capable of expressing the decoy polynucleotide, the binding of ZNF143 to the ZNF143-binding nucleotide sequence on the chromosome is inhibited, a function (transcription promoting activity) of ZNF143 is suppressed, and cancer cell proliferation is inhibited:

(1) the nucleotide sequence shown by SEQ ID NO:4; and
(2) a nucleotide sequence having an identity of 60% or more to the nucleotide sequence shown by SEQ ID NO:4, wherein the 4th, 5th, and 6th cytosines of the nucleotide sequence shown by SEQ ID NO:4 are conserved, and wherein the 13th nucleotide is cytosine or guanine.

Therefore, the above-described decoy polynucleotide and an expression vector capable of expressing the decoy polynucleotide are also preferred as substances that suppress a function of ZNF143 that can be contained in the agent of the present invention. As examples of suitable ZNF143-binding nucleotide sequences, the nucleotide sequences shown by any of SEQ ID NO:10 to 44 can be mentioned.

The ZNF143-binding nucleotide sequence shown by SEQ ID NO:4 is a ZNF143-binding nucleotide sequence that is commonly present in the promoters of gene groups that undergo upregulation by ZNF143. As preferred examples of the nucleotide sequence shown by SEQ ID NO:4, the 19 bases at the 3' end of the nucleotide sequence shown by any of SEQ ID NO:10 to 29, the nucleotide sequence shown by any of SEQ ID NO:30 to 44 and the like can be mentioned.

As suitable examples of the above-described decoy polynucleotide, polynucleotides (DNAs) comprising the nucleotide sequence shown by any of SEQ ID NO:10 to 44 can be mentioned.

As shown in an Example below, in the nucleotide sequences to which ZNF143 binds, the 4th, 5th, and 6th cytosines of the nucleotide sequence shown by SEQ ID NO:4 and the 13th cytosine or guanine are highly conserved, and even if nucleotides in any other portions are substituted, the influence on the ZNF143 binding activity is low. Therefore, a polynucleotide comprising a nucleotide sequence having an identity of 60% or more, preferably about 70% or more, more preferably about 80% or more, still more preferably about 90% or more, yet still more preferably about 95% or more, to the nucleotide sequence shown by SEQ ID NO:4, wherein the 4th, 5th, and 6th cytosines of the nucleotide sequence shown by SEQ ID NO:4 are conserved, and wherein the 13th nucleotide is cytosine or guanine, is also useful as a decoy polynucleotide. ZNF143 is capable of binding to the decoy polynucleotide under physiological conditions (for example, intracellular and the like); as a result, the binding of ZNF143 to the ZNF143-binding nucleotide sequence on the chromosome is inhibited, and a function (transcription promoting activity) of ZNF143 is suppressed.

The length of the above-described decoy polynucleotide, in view of the ease of synthesis, antigenicity issues and the like, is normally about 200 bases or less, preferably about 50 bases or less, more preferably about 30 bases or less.

Although the choice of decoy polynucleotide may be a DNA or an RNA, or may be a DNA/RNA chimera, and is normally a DNA. The decoy polynucleotide is single-stranded or double-stranded, preferably double-stranded. A natural-type decoy polynucleotide has the phosphoric acid diester linkage thereof easily decomposed by nucleases present in cells, so a decoy polynucleotide can also be synthesized using a modified nucleotide such as the thiophosphate type (P=O in phosphate linkage replaced with P=S), 2'-O-methyl type, or morpholino-oligo group modified type, which are stable to the decomposing enzymes.

A decoy polynucleotide can be synthesized using a commercially available automated DNA/RNA synthesizer (Applied Biosystems, Beckman and the like).

The present invention can also be embodied using an expression vector capable of expressing (that encodes) the above-described decoy polynucleotide. In the expression vector, normally, a nucleotide sequence that encodes the above-described decoy polynucleotide is functionally joined to a promoter capable of exhibiting promoter activity in the cells of the mammal that is the subject of administration. The other features of the expression vector are the same as those for the above-described expression vector capable of expressing the antisense polynucleotide.

The agent of the present invention, in addition to an effective amount of a substance that suppresses a function of ZNF143, can comprise an optionally chosen carrier, for example, a pharmaceutically acceptable carrier.

As examples of the pharmaceutically acceptable carrier, excipients such as sucrose, starch, mannitol, sorbitol, lactose, glucose, cellulose, talc, calcium phosphate and calcium carbonate; binders such as cellulose, methylcellulose, hydroxypropylcellulose, polypropylpyrrolidone, gelatin, acacia, polyethylene glycol, sucrose and starch; disintegrants such as starch, carboxymethylcellulose, hydroxypropyl starch, sodium-glycol-starch, sodium hydrogen carbonate, calcium phosphate and calcium citrate; lubricants such as magnesium stearate, Aerosil, talc and sodium lauryl sulfate; flavoring agents such as citric acid, menthol, glycyrrhizin ammonium salt, glycine and orange flour; preservatives such as sodium benzoate, sodium hydrogen sulfite, methyl paraben and propyl paraben; stabilizers such as citric acid, sodium citrate and acetic acid; suspending agents such as methylcellulose, polyvinylpyrrolidone and aluminum stearate; dispersing agents such as surfactants; diluents such as water, physiological saline and orange juice; base waxes such as cacao butter, polyethylene glycol and refined kerosene; and the like can be mentioned, which, however, are not to be construed as limiting.

Preparations suitable for oral administration are a liquid comprising an effective amount of the substance dissolved in a diluent like water or physiological saline, a capsule, sachet or tablet containing an effective amount of substance as a solid or granules, a suspension comprising an effective amount of the substance suspended in an appropriate dispersion medium, an emulsion comprising a solution of an effective amount of substance dispersed and emulsified in an appropriate dispersion medium, and the like.

As preparations suitable for parenteral administration (for example, subcutaneous injection, intramuscular injection, topical injection, intraperitoneal administration and the like), aqueous and non-aqueous isotonic sterile injectable liquids are available, which may contain an antioxidant, a buffer solution, a bacteriostatic agent, an isotonizing agent and the like. Also, aqueous and non-aqueous sterile suspensions can be mentioned, which may contain a suspending agent, a solubilizer, a thickener, a stabilizer, an antiseptic and the like. The preparation, like ampoules and vials, can be enclosed in a container for a unit dosage or a multiple dosage. Also, an active ingredient and a pharmaceutically acceptable carrier can also be freeze-dried and stored in a state that may be dissolved or suspended in an appropriate sterile vehicle just before use.

To promote the introduction of a polynucleotide or expression vector into a cell, the agent of the present invention can further comprise a reagent for polynucleotide introduction. When the polynucleotide is incorporated in a viral vector, particularly in a retrovirus vector, retronectin, fibronectin, polybrene or the like can be used as a reagent for polynucleotide introduction. When the polynucleotide is incorporated in a plasmid vector, an anionic lipid such as lipofectin, lipfectamine, DOGS (transfectam; dioctadecylamidoglycylspermine), DOPE (1,2-dioleoyl-sn-glycero-3-phosphoethanolamine), DOTAP (1,2-dioleoyl-3-trimethylammoniumpropane), DDAB (dimethyldioctadecylammonium bromide), DHDEAB (N,N-di-n-hexadecyl-N,N-dihydroxyethylammonium bromide), HDEAB (N-n-hexadecyl-N,N-dihydroxyethylammonium bromide), polybrene, or poly(ethyleneimine) (PEI), or calcium phosphate can be used.

The dosage and method or means of administration of the agent of the present invention can be chosen as appropriate according to the kind of activity, severity of illness, therapeutic policy, patient age, body weight, sex, overall health condition, and patient (hereditary) racial background by those skilled in the art. For example, when the above-described antisense polynucleotide or decoy polynucleotide is administered to an adult, the dosage is about 0.1 to 100 mg/day/person.

The agent of the present invention can be intended for inhibition of cancer cell proliferation (cancer cell proliferation inhibitor). By suppressing a function of ZNF143 using the agent of the present invention, the proliferation of the cells of a target cancer (for example, colorectal cancer, lung cancer (adenocarcinoma), ovarian cancer, breast cancer, gall bladder cancer, prostatic cancer, uterine cervical cancer and the like) is suppressed. Therefore, the agent of the present invention is useful as a prophylactic or therapeutic drug for a target cancer (for example, colorectal cancer, lung cancer (adenocarcinoma), ovarian cancer, breast cancer, gall bladder cancer, prostatic cancer, uterine cervical cancer and the like).

(2. Detection of Cancer Using ZNF143)

The present invention provides a method of detecting a cancer cell in a tissue (the detection method of the present invention), comprising measuring the ZNF143 expression level in the tissue, and determining whether or not a cancer cell is contained in the tissue on the basis of the expression level.

Kinds of tissues that can be used in the detection method of the present invention include, but are not limited to, the large intestine, lung, ovary, mammary gland, gall bladder, uterus and the like derived from the aforementioned mammals (humans, mice and the like). By using a tissue separated from a living organism, the detection method of the present invention can be performed in vitro.

In the detection method of the present invention, the expression level of the ZNF143 polypeptide or a polynucleotide (for example, mRNA, preferably mature mRNA) that encodes the polypeptide in various tissues is measured.

The expression level of the ZNF143 polypeptide can be measured by an immunological technique using an antibody that specifically recognizes ZNF143, for example, an antibody that specifically recognizes a polypeptide consisting of the amino acid sequence shown by SEQ ID NO:7 or 9. As the immunological technique, flow cytometric analysis, radioimmunoassay method (RIA method), ELISA method (Methods in Enzymol. 70: 419-439 (1980)), Western blotting, immunohistological staining and the like can be mentioned.

An antibody that specifically recognizes ZNF143 can be produced by an existing ordinary method of production using the ZNF143 polypeptide or a partial peptide thereof possessing antigenicity as an immunogen. As mentioned herein, antibodies include, but are not limited to, natural type antibodies such as polyclonal antibodies and monoclonal antibodies (mAbs), chimeric antibodies, humanized antibodies, and single-stranded antibodies that can be produced using gene recombination technology, and binding fragments thereof. Preferably, the antibody is a polyclonal antibody, monoclonal antibody or a binding fragment thereof. A binding fragment means a partial region of one of the above-described antibodies possessing specific binding activity; specifically, for example, F(ab')$_2$, Fab', Fab, Fv, sFv, dsFv, sdAb and the like can be mentioned (Exp. Opin. Ther. Patents, Vol. 6, No. 5, p. 441-456, 1996). The class of the antibody is not particularly limited; antibodies of any isotypes such as IgG, IgM, IgA, IgD and IgE are encompassed. Preferably, the class is IgG or IgM, and in view of the ease of purification and the like, IgG is more preferable.

The expression level of a polynucleotide that encodes ZNF143 can be measured by a method known per se using a nucleic acid probe or primer capable of specifically detecting the polynucleotide, for example, (i) a nucleic acid probe or primer capable of specifically detecting a polynucleotide consisting of the nucleotide sequence shown by SEQ ID NO:6 or 8, or (ii) a nucleic acid probe or primer capable of specifically detecting a polynucleotide consisting of a nucleotide sequence that encodes a polypeptide consisting of the amino acid sequence shown by SEQ ID NO:7 or 9. As examples of the measuring method, RT-PCR, Northern blotting, in situ hybridization, cDNA array and the like can be mentioned.

In one preferred embodiment, the nucleic acid probe used in the detection method of the present invention is a polynucleotide comprising a nucleotide sequence of a streak of about 15 bases or more, preferably about 18 to about 500 bases, more preferably about 18 to about 200 bases, still more preferably about 18 to about 50 bases, or a sequence complementary thereto, contained in the nucleotide sequence shown by SEQ ID NO:6 or 8, or the nucleotide sequence that encodes a polypeptide consisting of the amino acid sequence shown by SEQ ID NO:7 or 9.

In another preferred embodiment, the nucleic acid probe used in the detection method of the present invention is a polynucleotide comprising the nucleotide sequence shown by SEQ ID NO:6 or 8, or a nucleotide sequence that hybridizes under stringent conditions with a nucleotide sequence that encodes a polypeptide consisting of the amino acid sequence shown by SEQ ID NO:7 or 9. The hybridization can be performed according to a method known per se or a method based thereon, for example, the method described in Molecular Cloning, 2nd edition (J. Sambrook et al., Cold Spring Harbor Lab. Press, 1989) and the like. Examples of stringent conditions include those wherein a hybridization reaction at 45° C. in 6×SSC (sodium chloride/sodium citrate) is followed by one time or more of washing at 65° C. in 0.2×SSC/0.1% SDS and the like. Those skilled in the art are able to easily obtain desired stringency by changing the salt concentration of the hybridization solution, hybridization reaction temperature, probe concentration, probe length, the number of mismatches, hybridization reaction time, the salt concentration of the washing solution, washing temperature and the like as appropriate. The length of the nucleic acid probe is normally about 15 bases or more, preferably about 18 to about 500 bases, more preferably about 18 to about 200 bases, still more preferably about 18 to about 50 bases.

The nucleic acid probe may comprise an additional sequence (a nucleotide sequence not complementary to the polynucleotide which is the subject of detection), as far as the specific detection is not interfered with.

The nucleic acid probe may be previously labeled with an appropriate labeling agent, for example, a radioisotope (examples: $^{125}$I, $^{131}$I, $^{3}$H, $^{14}$C, $^{32}$P, $^{33}$P and the like), an enzyme (examples: β-galactosidase, β-glucosidase, alkaline phosphatase, peroxidase, malate dehydrogenase and the like), a fluorescent substance (examples: fluorescamine, fluorescein isothiocyanate and the like), a luminescent substance (examples: luminol, luminol derivative, luciferin, lucigenin and the like) and the like. Alternatively, in the vicinity of a fluorescent substance (examples: FAM, VIC and the like), a quencher (quenching substance) that absorbs the fluorescence energy produced by the fluorescent substance may further be bound. In this mode of embodiment, upon the detection reaction, the fluorescent substance and the quencher become separated from each other and fluorescence is detected.

The nucleic acid primer used in the detection method of the present invention may be any one, as far as it is designed to be capable of specifically amplifying a partial or the entire region of a polynucleotide consisting of the nucleotide sequence shown by SEQ ID NO:6 or 8, or a nucleotide sequence that encodes a polypeptide consisting of the amino acid sequence shown by SEQ ID NO:7 or 9. For example, a pair of polynucleotides can be mentioned, which is a combination of a polynucleotide comprising a nucleotide sequence of about 15 to about 50 bases, preferably about 18 to about 30 bases, that hybridizes with a portion of a sequence complementary to the above-described nucleotide sequence, and a polynucleotide comprising a nucleotide sequence of about 15 to about 50 bases, preferably about 18 to about 30 bases, that hybridizes with a portion of the above-described nucleotide sequence on the 3' side from this hybridization site, wherein the length of the nucleic acid fragment amplified thereby is about 50 to about 1,000 bases, preferably about 50 to about 500 bases, more preferably about 50 to about 200 bases.

The nucleic acid primer may comprise an additional sequence (a nucleotide sequence not complementary to the polynucleotide which is the subject of detection), as far as the specific detection is not interfered with.

The nucleic acid primer may be previously labeled with an appropriate labeling agent, for example, a radioisotope (examples: $^{125}$I, $^{131}$I, $^{3}$H, $^{14}$C, $^{32}$P, $^{33}$P and the like), an enzyme (examples: β-galactosidase, β-glucosidase, alkaline phosphatase, peroxidase, malate dehydrogenase and the like), a fluorescent substance (examples: fluorescamine, fluorescein isothiocyanate and the like), a luminescent substance (examples: luminol, luminol derivative, luciferin, lucigenin and the like) and the like.

The nucleic acid probe or primer may be a DNA or an RNA, and may be single-stranded or double-stranded. In the case of a double-strand, it may be any of a double-stranded DNA, a double-stranded RNA, and a DNA/RNA hybrid.

The above-described nucleic acid probe or primer can be synthesized on the basis of, for example, information on the nucleotide sequence shown by SEQ ID NO:6 or 8 using a commercially available automated DNA/RNA synthesizer (Applied Biosystems, Beckman and the like) according to a conventional method.

Next, on the basis of the measured expression level of ZNF143, whether or not a cancer cell is contained in the tissue is determined. As shown in an Example below, the ZNF143 expression level is higher in cancer cells than in normal cells, so if a cancer cell is contained in the tissue, the measured ZNF143 expression level rises. The above-described determination is made on the basis of this correlation between the ZNF143 expression level and the presence or absence of a cancer cell in the tissue.

For example, a normal tissue not containing a cancer cell (negative control) and a tissue containing a cancer cell (positive control) are provided, and the ZNF143 expression level in a tissue extirpated from the subject patient is compared with the levels in the positive control and negative control. Alternatively, a correlation chart of the ZNF143 expression level in a tissue and the presence or absence of a cancer cell may be generated in advance, and the ZNF143 expression level in a tissue extirpated from the subject patient may be compared with the correlation chart. The comparison of expression levels is preferably made on the basis of the presence or absence of a significant difference.

When the ZNF143 expression level of the subject of measurement is relatively high based on the comparison results of ZNF143 expression levels, it can be judged that the possibility of containment of a cancer cell in the tissue is relatively high. Conversely, if the ZNF143 expression level in the subject of measurement is relatively low, it can be judged that the possibility of containment of a cancer cell in the tissue is relatively low.

The rating can also be made by previously setting a cutoff value for ZNF143 expression levels, and comparing the measured ZNF143 expression level and this cutoff value. For example, if the measured ZNF143 expression level is not less than the aforementioned cutoff value, it can be judged that the possibility of containment of a cancer cell in the tissue is relatively high. Conversely, if the ZNF143 expression level is lower than the cutoff value, it can be judged that the possibility of containment of a cancer cell in the tissue is relatively low. "A cutoff value" is a value that meets the requirements for both high diagnostic sensitivity (true positive rate) and high diagnostic specificity (true negative rate) when a disease or condition is rated with that value as a criterion. For example, a ZNF143 expression level that produces high positivity rates in tissues containing a cancer cell, and high negativity rates in tissues not containing a cancer cell, can be set as a cutoff value.

The present invention also provides a nucleic acid probe or primer capable of specifically detecting the above-described polynucleotide that encodes ZNF143, or a diagnostic reagent for cancer comprising an antibody that specifically recognizes ZNF143. The diagnostic reagent of the present invention can be a kit for determining whether or not a cancer cell is contained in a tissue. By using the diagnostic reagent of the present invention, it is easily possible to determine whether or not a cancer cell is contained in a tissue by the above-described method.

The diagnostic reagent of the present invention may further contain other ingredients required for embodying the method, depending on the method of measuring the expression level of ZNF143.

For example, provided that the diagnostic reagent of the present invention comprises an antibody that specifically recognizes ZNF143, it is possible to determine whether or not a cancer cell is contained in a tissue by measuring the ZNF143 expression level using an immunological technique. In this case, the diagnostic reagent of the present invention can further contain a labeled secondary antibody, a color developing substrate, a blocking liquid, a washing buffer solution, an ELISA plate, a blotting membrane and the like.

Provided that the diagnostic reagent of the present invention comprises a nucleic acid probe or primer capable of specifically detecting a polynucleotide that encodes ZNF143, it is possible to determine whether or not a cancer cell is contained in a tissue by measuring the ZNF143 expression level by RT-PCR, Northern blotting, in situ hybridization, cDNA array and the like. When RT-PCR is used in the measurement, the diagnostic reagent of the present invention can further contain a 10×PCR reaction buffer solution, a 10×MgCl$_2$ aqueous solution, a 10×dNTPs aqueous solution, Taq DNA polymerase (5 U/µL), reverse transcriptase and the like. When Northern blotting or a cDNA array is used in the measurement, the diagnostic reagent of the present invention can further contain a blotting buffer solution, a labeling reagent, a blotting membrane and the like. When in situ hybridization is used in the measurement, the diagnostic reagent of the present invention can further contain a labeling reagent, a color developing substrate and the like.

(3. Vector Comprising a Polynucleotide to which ZNF143 Binds)

The present invention provides a vector having a nucleotide sequence wherein a nucleotide sequence that encodes a monitoring gene is functionally joined downstream of the above-described ZNF143-binding nucleotide sequence. The vector of the present invention is useful in the screening method of the present invention described below.

As the monitoring gene, proteins permitting easy detection of the expression thereof (luminescent/fluorescent gene groups (for example, GFP (green fluorescent protein) gene, GUS (β-glucuronidase) gene, LUC (luciferase) gene, CAT (chloramphenicol acetyltransferase) gene)) can be mentioned; although there is no limitation, preference is given to luminescent gene luciferase. Vectors are publicly known in the technical field; for example, the vectors mentioned in the foregoing section (1. Inhibition of cancer cell proliferation by suppression of function of ZNF143) can be used. A commercially available vector having a monitoring gene already integrated therein may be used.

In the vector of the present invention, a nucleotide sequence that encodes a monitoring gene is functionally joined downstream of the ZNF143-binding nucleotide sequence. "Functional joining" refers to a mode of joining such that the ZNF143-binding nucleotide sequence acts as a promoter of the monitoring gene in cells to induce the expression of the monitoring gene upon the binding of ZNF143 to the ZNF143-binding nucleotide sequence. Normally, the ZNF143-binding nucleotide sequence is placed at the 5' of the monitoring gene. The distance between the ZNF143-binding nucleotide sequence and the initiation codon of the monitoring gene is normally 20 to 150 bp, and is not particularly limited, as far as "functional joining" is achieved. The nucleotide sequence interposing between the ZNF143-binding nucleotide sequence and the transcription initiation point of the monitoring gene is also not particularly limited, as far as "functional joining" is achieved.

In the vector of the present invention, the number of copies of the ZNF143-binding nucleotide sequence contained in one vector is not particularly limited; only 1 copy of the ZNF143-binding nucleotide sequence may be contained in one vector, or a plurality of copies of the ZNF143-binding nucleotide sequence may be contained in a tandemly joined state in one vector. By using a plurality of copies of the ZNF143-binding nucleotide sequence is used in tandem joining, it is possible to more potently induce the expression of a monitoring gene, and the detection sensitivity for the monitoring gene increases in the screening described below. When a plurality of copies of ZNF143-binding nucleotide sequence are used in tandem joining, the number of copies of ZNF143-binding nucleotide sequence joined is not particularly limited, and is, for example, about 2 to 50 copies, preferably 2 to 20 copies, more preferably 2 to 10 copies. In view of the ease of polynucleotide joining operation and the like, a number of approximately 2 to 5 copies is preferred.

When a plurality of copies of ZNF143-binding nucleotide sequence are used in tandem joining, the individual ZNF143-binding nucleotide sequences may be identical or not. The ZNF143-binding nucleotide sequences may be joined together adjacently (i.e., without being mediated by a spacer region), or may be joined via a spacer region. Although the length of the spacer region is not particularly limited, as far as all constituents from the monitoring gene to the plurality of copies of ZNF143-binding nucleotide sequence joined can be stably present, without interruption, in one vector, and the expression of the monitoring gene can be induced dependently on the binding of ZNF143, it is preferable that the length be up to 1 Kbp, for example, 5 Kbp or less, 3 Kbp or less, 1 Kbp or less, 500 by or less, 200 by or less, 100 by or less, 50 by or less, and 25 by or less. The nucleotide sequence that constitutes the spacer region is not particularly limited, and may be an optionally chosen sequence.

The vector of the present invention may contain an enhancer, a splicing signal, a poly A addition signal, a selection marker, an SV40 replication origin (hereinafter, also abbreviated as SV40ori) and the like in respective functional ways as desired. As examples of the selection marker, the dihydrofolate reductase (hereinafter, also abbreviated as dhfr) gene [methotrexate (MTX) resistance], the ampicillin resistance gene (hereinafter, also abbreviated as Amp$^r$), the neomycin resistance gene (hereinafter, also abbreviated as Neo$^r$, G418 resistance) and the like can be mentioned.

By introducing the vector of the present invention into a cell according to a method of gene transfer known per se (for example, lipofection method, calcium phosphate method, microinjection method, protoplast fusion method, electroporation method, DEAE dextran method, gene transfer using gene gun, and the like), a cell transformed with the vector (the cell of the present invention) can be produced. The cell is useful in the screening method of the present invention described below.

As examples of the cell, bacteria of the genus *Escherichia* (*Escherichia coli* and the like), bacteria of the genus *Bacillus* (*Bacillus subtilis* and the like), yeasts (*Saccharomyces cerevisiae* and the like), insect cells (established cells derived from fall armyworm larva (*Spodoptera frugiperda* cell; Sf cell) and the like), mammalian cells and the like are used. The cell is preferably a mammalian cell.

As the mammalian cell, cancer cell lines, primary culture cells and the like can be mentioned; although the kind thereof is not particularly limited, normally a cancer cell (PC3 cell and the like) is used.

As examples of the mammal, laboratory animals such as rodents such as mice, rats, hamsters, and guinea pigs, and rabbits; domestic animals such as pigs, bovines, goat, horses, sheep and minks; companion animals such as dogs and cats; primates such as humans, monkeys, rhesuses, marmosets, orangutans, and chimpanzees; and the like can be mentioned.

It is preferable that the cell be expressing ZNF143. When the above-described vector is incorporated in the cell expressing ZNF143, the ZNF143 binds to the ZNF-binding nucleotide sequence on the vector, and the monitoring gene is expressed ZNF143-dependently. Because cancer cells normally express ZNF143 at high levels, it is preferable from this viewpoint as well that the vector of the present invention be introduced into a cancer cell.

(4. Screening Method for Substance Possessing Cancer Cell) Proliferation Inhibitory Activity As stated above, a substance that suppresses a function of ZNF143 is capable of inhibiting cancer cell proliferation to prevent and/or treat cancer. Therefore, by selecting a substance that suppresses a function of ZNF143, it is possible to acquire a substance that inhibits cancer cell proliferation or a substance for preventing and/or treating cancer.

The substance subjected to the screening method may be any commonly known compound or a novel compound; examples include nucleic acids, glucides, lipids, proteins, peptides, organic low molecular compounds, compound libraries prepared using combinatorial chemistry technology, random peptide libraries prepared by solid phase synthesis or the phage display method, or naturally occurring ingredients derived from microorganisms, animals, plants, marine organisms and the like.

For example, a cell permitting a measurement of the expression or a function of ZNF143 is cultured in the presence of a test substance, measuring the expression amount or function of ZNF143 in the cell cultured in the presence of the test substance, and comparing the expression amount or function with the expression amount or function of ZNF143 in a control cell cultured in the absence of the test substance.

A cell permitting a measurement of the expression of ZNF143 refers to a cell enabling a direct or indirect evaluation of the expression level of a product, for example, transcription product or translation product, of the ZNF143 gene. A cell enabling a direct evaluation of the expression level of a product of the ZNF143 gene can be a cell capable of naturally expressing ZNF143, whereas a cell enabling an indirect evaluation of the expression level of a product of the ZNF143 gene can be a cell permitting a reporter assay of the transcriptional regulatory region of the ZNF143 gene.

The cell capable of naturally expressing ZNF143 is not particularly limited, as far as it potentially expresses ZNF143. Such cells can easily be identified by those skilled in the art, and cells in primary culture, a cell line derived from primary culture cells, a commercially available cell line, a cell line available from a cell bank, and the like can be used. As examples of the cell capable of naturally expressing ZNF143, colorectal cancer cells, ovarian cancer cells, embryo cancer cells, breast cancer cells, gall bladder cancer cells, prostatic cancer cells, uterine cervical cancer cells and the like of the aforementioned mammals can be mentioned.

The cell permitting a reporter assay for the transcriptional regulatory region of the ZNF143 gene is a cell comprising the transcriptional regulatory region of the ZNF143 gene and a reporter gene functionally joined to the region. The transcriptional regulatory region of the ZNF143 gene and the reporter gene can be inserted into an expression vector. The transcriptional regulatory region of the ZNF143 gene is not particularly limited, as far as the region is capable of controlling the expression of the ZNF143; examples include a region between the transcription initiation point and about 2 kbp upstream thereof, a region consisting of a base sequence resulting from deletion, substitution or addition of 1 or more bases in the base sequence of the region, and having the capability of controlling the transcription of the ZNF143 gene, and the like. The reporter gene may be any gene that encodes an enzyme that catalyzes the production of a detectable protein or a detectable substance; examples include the GFP (green fluorescence protein) gene, GUS (β-glucuronidase) gene, LUC (luciferase) gene, CAT (chloramphenicol acetyltransferase) gene and the like.

As a cell permitting a measurement of a function of ZNF143, the above-described cell of the present invention can be mentioned. In the cell, the ZNF143 function level can be evaluated with the expression amount of a monitoring gene as an index; if a function of ZNF143 is inhibited, the expression amount of the monitoring gene decreases.

Next, the expression amount or a function of ZNF143 in cells subcultured in the presence of a test substance is measured. This measurement of the expression amount or function can be performed by a method known per se, in view of the choice of cells used and the like. For example, when a cell capable of naturally expressing ZNF143 are used as a cell permitting a measurement of the expression of ZNF143, the expression amount can be measured by a method known per se on a product, for example, a transcription product (mRNA) or translation product (polypeptide), of the ZNF143 gene. For example, the expression amount of transcription product can be measured by RT-PCR, Northern blotting and the like using a total RNA prepared from the cells. The expression amount of translation product can be measured by an immunological technique using an extract prepared from the cells. As the immunological technique, radioimmunoassay method (RIA method), ELISA method (Methods in Enzymol. 70: 419-439 (1980)), fluorescent antibody method, Western blotting method and the like can be used. Meanwhile, when a cell permitting a reporter assay for the transcriptional regulatory region of the ZNF143 gene are used as a cell permitting a measurement of the expression of ZNF143, the expression amount can be measured on the basis of the signal intensity of the reporter. When the above-described cell of the present invention is used as a cell permitting a measurement of a function of ZNF143, the function of ZNF143 is evaluated as an expression amount of monitoring gene.

Subsequently, the expression amount or a function of ZNF143 in the cell cultured in the presence of the test substance is compared with the expression amount or function of ZNF143 in a control cell cultured in the absence of the test substance. This comparison of the expression amounts is preferably performed on the basis of the presence or absence of a significant difference. Although the expression amount or function of ZNF143 in the control cell not contacted with the test substance may be measured before or simultaneously with the measurement of the expression amount of ZNF143 in the cell contacted with the test substance, it is preferable, from the viewpoint of experimental accuracy and reproducibility, that the former amount be a simultaneously measured amount.

A compound judged as a result of the comparison to suppress the expression or function of ZNF143 can be selected as a substance capable of inhibiting cancer cell proliferation or a substance capable of preventing and/or treating cancer.

In a preferred embodiment, the screening method of the present invention comprises the steps of:
(a) culturing cells transformed with a vector having a nucleotide sequence wherein a nucleotide sequence that encodes a monitoring gene is functionally joined downstream of a ZNF143-binding nucleotide sequence in the presence of a test substance, (b) measuring the expression amount of the monitoring gene in the cells cultured in the presence of the test substance, and comparing the expression amount with the expression amount in control cells cultured in the absence of the test substance, and (c) selecting a test substance that suppresses the expression amount of the monitoring gene as a substance capable of inhibiting cancer cell proliferation on the basis of the result of the comparison (b).

The substance that can be obtained by the screening method of the present invention can serve as a candidate compound for pharmaceutical development, and can be prepared as a cancer cell proliferation inhibitor or a prophylactic and/or therapeutic drug for cancer as with the above-described agent of the present invention.

The present invention is hereinafter described more specifically by means of the following Examples, by which, however, the invention is not limited in any way.

EXAMPLES

Example 1

Expression Analysis with DNA Array

Expression profile analysis by the RNA interference method was performed using a lung cancer cell line. Specifically, an siRNA consisting of the nucleotide sequence shown by SEQ ID NO:1 described hereinabove was transfected to a lung cancer cell line using Invitrogen Lipofectamine 2000 and Opti-MEM medium, and the cells were cultured for 3 days, after which expression analysis was performed with a DNA array. As a result, the ZNF143 gene was found to control the transcriptional regulation of at least 20 or more molecules in a group of molecules that positively control the cell cycle. From this finding, it was estimated that the ZNF143 gene has a property as a master gene.

There were about 150 genes controlled to have an expression ratio of 0.4 or less compared with the expression amount in the cells cultured in the absence of the siRNA (SEQ ID NO:1). Of them, the genes listed in Table 1 were found to be essential to cell proliferation.

TABLE 1

| Name of gene | ZNF143-binding nucleotide sequence |
| --- | --- |
| AURKB | SEQ ID NO: 10 |
| CDC2L6 | SEQ ID NO: 11, 12 |
| CDK2 | SEQ ID NO: 13 |
| RFC2 | SEQ ID NO: 14 |
| CCNA2 | SEQ ID NO: 15 |
| CDC6 | SEQ ID NO: 16 |
| CDCA5 | SEQ ID NO: 17 |
| CDT1 | SEQ ID NO: 18, 34 |
| GTSE1 | SEQ ID NO: 19 |
| PFS2 | SEQ ID NO: 20 |
| RFC4 | SEQ ID NO: 21 |
| WEE1 | SEQ ID NO: 22 |
| CDCA3 | SEQ ID NO: 23 |
| CDCA8 | SEQ ID NO: 24, 25 |
| MCM2 | SEQ ID NO: 26 |
| PLK1 | SEQ ID NO: 27, 43 |
| SPBC25 | SEQ ID NO: 28 |
| ZNF367 (CDC14B) | SEQ ID NO: 29 |

Next, the nucleotide sequences of the genes listed in Table 1 were searched for from human genome information, and the base sequences of the promoter portions were confirmed at the same time. As a result, promoter nucleotide sequence analysis revealed that all these genes have a ZNF143-binding site in the core promoter region. The ZNF143-binding nucleotide sequences present in the promoter regions of the respective genes are shown in Table 1. Of these nucleotide sequences, those shown by SEQ ID NO:10 to 29 possess binding activity for ZNF143 even without the 5'-terminal 6-base nucleotide. The involvement of the ZNF143-binding nucleotide sequences listed in Table 1 in the expressional regulation of each gene by ZNF143 was demonstrated by the gel shift method and the chromatin immunoprecipitation method.

In the gel shift method, DNAs consisting of the above-described ZNF143-binding nucleotide sequences (SEQ ID NO:10 to 44) and the ZNF143 protein as produced by the recombinant method were used after purification. This led to the demonstration by in vitro experiments that ZNF143 binds to the above-described ZNF143-binding nucleotide sequences.

In the chromatin immunoprecipitation method, it was actually confirmed that a conjugate of ZNF143 polypeptide/ZNF143-binding nucleotide sequence was present in the cells.

The specific procedures are as follows.

1) Because the cells produce the ZNF143 polypeptide, a ZNF143 polypeptide/gene conjugate is present in the cells.
2) Couple the protein and DNA covalently using formaldehyde.
3) Destroy the cells and collect the nuclear (chromatin) fraction.
4) Disrupt the DNA using ultrasound.
5) Immunoprecipitate the DNA with anti-ZNF143 antibody.
6) Extract the DNA.
7) Separately, previously design primers that flank the binding nucleotide sequence of the promoter portion as confirmed on the basis of genome information on the target gene.
8) Amplify the nucleotide sequence by a PCR method using the primers.
9) Confirm the presence of PCR product by agarose gel electrophoresis.

The results of the above-described analysis suggested that ZNF143 might bind to the nucleotide sequence shown by SEQ ID NO:4 in the promoter region of a gene to regulate the expression of the gene.

Example 2

FACS Analysis of Cells Incorporating ZNF143-Specific siRNA

The cell cycle of a prostatic cancer cell line PC3 was analyzed by FACS 72 hours after introduction of a ZNF143-specific siRNA (SEQ ID NO:1). The results are shown in Table 2. The numerical figures in the Table are percent ratios of cell count in each phase to total cell count. In this analysis, cell accumulation in the G2/M phase was observed, and the emergence of a subG1 fraction was noted. Therefore, it was found that introduction of the siRNA against ZNF143 into the cells completely suppresses cancer cell proliferation, resulting in the termination of the cell cycle in the G2/M phase.

TABLE 2

|  | Cell cycle | | | | Annexin V staining |
|---|---|---|---|---|---|
|  | G1 | S | G2/M | subG1 |  |
| Mock | 54.0 | 19.4 | 24.0 | 1.03 | 6.3 |
| Control siRNA | 55.7 | 16.9 | 21.9 | 0.93 | 6.0 |
| ZNF143 siRNA1 | 43.6 | 16.5 | 33.9 | 4.47 | 11.6 |
| ZNF143 siRNA2 | 39.5 | 10.2 | 42.9 | 5.22 | 13.1 |

Example 3

Immunohistological Staining of Clinical Cancer Samples

Formalin-fixed paraffin-embedded sections of typical cancer tissues were immunologically stained using a polyclonal antibody, the dextran polymer method and diaminobenzidine (DAB) (Kohno Y. et al. Brit. J. Cancer 2006, 94, p710 to 716).

Figure 4:
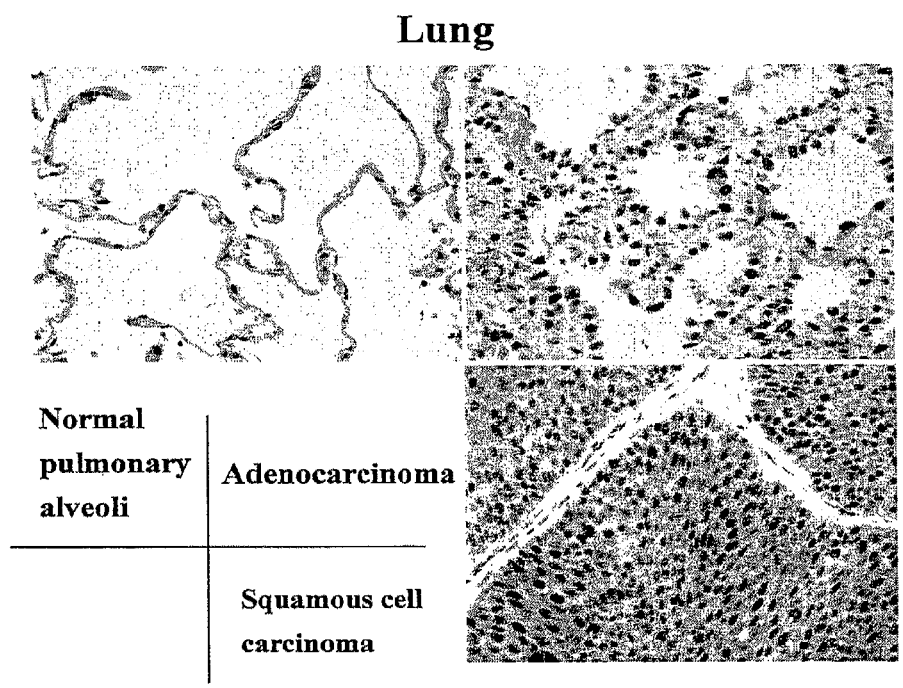
FIG. 4 shows immunohistologically stained images of clinical cancer samples (lung cancer) stained in Example 2.

The cancer tissues used were clinical samples of colorectal cancer, lung cancer (adenocarcinoma), ovarian cancer, breast cancer, gall bladder cancer and uterine cervical cancer, which are representative proliferative diseases. As a result, it was found that ZNF143 was expressed at low levels in normal cells and overexpressed in the cancer cells. Results of staining are shown in FIGS. 2 to 4. The anti-ZNF143 polypeptide antibody used in this analysis was a rabbit polyclonal antibody supplied by Dr. G. R. Kunkel (Texas A&M University) (Rincon J. C. et al. Nucleic Acids Res. 1998, 21, p4846 to 4852).

Example 4

Suppression of Proliferation of Cells Incorporating ZNF143-Specific siRNA

Figure 5:
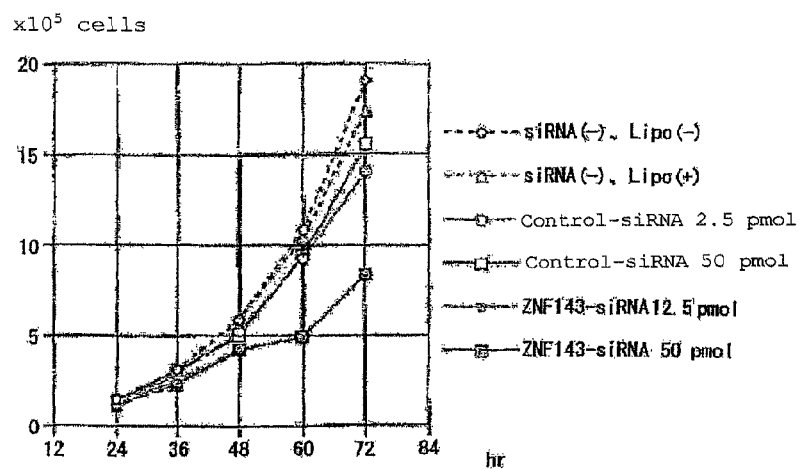
FIG. 5 is a graphic representation showing suppression of the proliferation of cells incorporating a ZNF143-specific siRNA (lung cancer cell nucleus A549).
Figure 6:
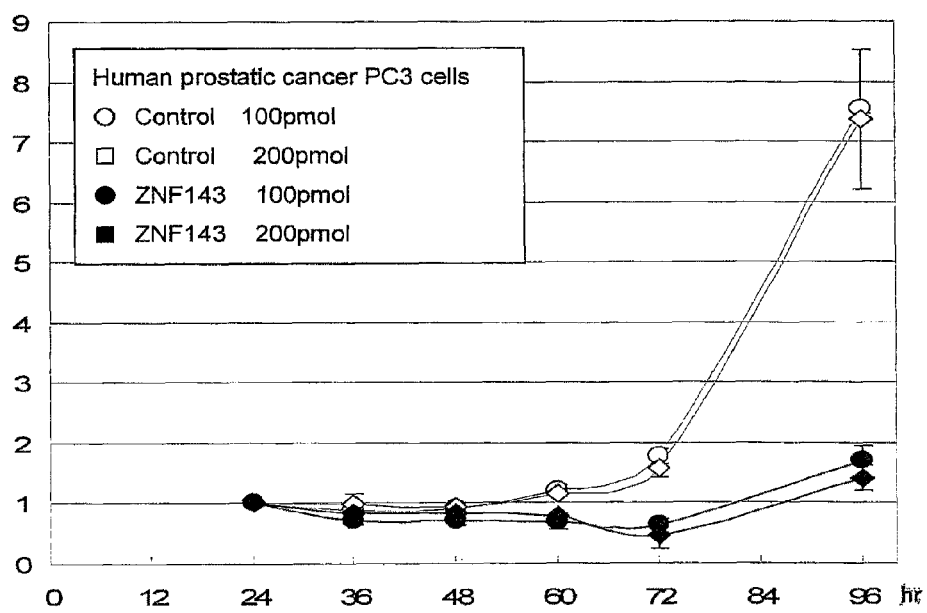
FIG. 6 is a graphic representation showing suppression of the proliferation of cells incorporating a ZNF143-specific siRNA (prostatic cancer PC3).

An siRNA consisting of the nucleotide sequence shown by SEQ ID NO:1 and a non-specific siRNA (control siRNA by Invitrogen) were introduced into the lung cancer cell line A549 and the prostatic cancer cell line PC3 using Invitrogen Lipofectamine 2000 and Opti-MEM medium. The results for the lung cancer cell line A549 are shown in FIG. 5; the results for the prostatic cancer cell line PC3 are shown in FIG. 6. As a result of cultivation, the cells incorporating the specific siRNA suppressed cell proliferation more potently than the cells incorporating the non-specific siRNA.

Example 5

Compound Screening System

A synthetic DNA prepared by joining two ZNF143-binding base sequences shown by SEQ ID NO:16 in tandem was inserted upstream of the luminescence gene of pGL3 (a vector having luminescence gene luciferase). This plasmid was transferred to prostatic cancer PC3 cells to establish cells that permanently express luciferase. The established cells express luciferase dependently on the ZNF143 gene. When an siRNA consisting of the nucleotide sequence shown by SEQ ID NO:3 and a non-specific siRNA (control siRNA of Invitrogen) were separately applied to this culture system, the expression of luciferase was suppressed and the luminescence decreased in the case of the siRNA (SEQ ID NO:3), whereas no change was seen in the case of the non-specific siRNA.

Industrial Applicability

Because the ZNF143 gene controls the expression of genes that are important to the progression of the cell cycle and DNA repair, a functional inhibition thereof is estimated to terminate the cell cycle of cancer cells in the G2 phase, and to inhibit DNA repair. Hence, the ZNF143 gene is thought to be an ideal molecular target for drug discovery capable of potently causing a functional inhibition of the G2 phase checkpoint.

This application is based on a patent application No. 2007-341430 filed in Japan (filing date: Dec. 28, 2007), the contents of which are incorporated in full herein.

The invention claimed is:

1. A method of inhibiting cancer cell proliferation in a mammal, which method comprises suppressing a function of ZNF143 by administering an effective amount of an agent consisting of a polynucleotide, which is a nucleotide that induces an RNA interference that targets a ZNF143 gene or antisense nucleotide that targets the ZNF143 gene and which comprises a nucleotide sequence complementary to a nucleotide sequence that encodes ZNF143 or a partial sequence thereof with 15 consecutive bases or more, or an expression vector capable of expressing the polynucleotide, and a pharmaceutically acceptable carrier to a cancer cell of the mammal.

2. The method according to claim 1, wherein the nucleotide that induces an RNA interference is siRNA and shRNA.

3. The method according to claim 1, wherein the polynucleotide is a double-stranded RNA comprising a nucleotide sequence complementary to the nucleotide sequence shown by SEQ ID NO: 6 or 8 or a partial sequence thereof with 21 consecutive bases or more.

4. The method according to claim 1, wherein the polynucleotide is a double-stranded RNA comprising a polynucleotide comprising the nucleotide sequence shown by any of SEQ ID NO: 1 to 3 or a partial sequence thereof with 21 to 30 consecutive bases, and a polynucleotide complementary to the polynucleotide.

5. A method of inhibiting cancer cell proliferation in a mammal, which method comprises suppressing a function of ZNF143 by administering an effective amount of an agent consisting of a polynucleotide comprising any ZNF143-binding nucleotide sequence selected from among the following nucleotide sequences, or an expression vector capable of expressing the polynucleotide, and a pharmaceutically acceptable carrier to a cancer cell of a mammal:

(1) the nucleotide sequence shown by SEQ ID NO: 4; and
(2) a nucleotide sequence having an identity of 60% or more to the nucleotide sequence shown by SEQ ID NO: 4, wherein the 4th, 5th, and 6th cytosines of the nucleotide sequence shown by SEQ ID NO: 4 are conserved, and wherein the 13th nucleotide is cytosine or guanine.

6. The method according to claim 1, wherein the cancer is selected from the group consisting of colorectal cancer, lung cancer, ovarian cancer, breast cancer, gall bladder cancer, prostatic cancer and uterine cervical cancer.

7. The method according to claim 5, wherein the cancer is selected from the group consisting of colorectal cancer, lung cancer, ovarian cancer, breast cancer, gall bladder cancer, prostatic cancer and uterine cervical cancer.

8. The method according to claim 1, which method terminates the cell cycle of cancer cells in the G2 phase.

9. The method according to claim 5, which method terminates the cell cycle of cancer cells in the G2 phase.

10. A therapeutic method for cancer comprising administering an effective amount of the agent consisting of a polynucleotide, which is a nucleotide that induces an RNA interference that targets a ZNF143 gene or antisense nucleotide that targets the ZNF143 gene and which comprises a nucleotide sequence complementary to a nucleotide sequence that encodes ZNF143 or a partial sequence thereof with 15 consecutive bases or more, or an expression vector capable of expressing the polynucleotide and a pharmaceutically acceptable carrier.

11. The method according to claim 10, wherein the nucleotide that induces an RNA interference is siRNA or shRNA.

12. The method according to claim 10, wherein the polynucleotide is a double-stranded RNA comprising the nucleotide sequence complementary to the nucleotide sequence shown by any of SEQ ID NO: 6 to 8 or a partial sequence thereof with 21 consecutive bases or more.

13. The method according to claim 10, wherein the polynucleotide is a double-stranded RNA comprising a polynucleotide comprising the nucleotide sequence shown by any of SEQ ID NO: 1 to 3 or a partial sequence thereof with 21 to 30 consecutive bases, and a polynucleotide complementary to the polynucleotide.

14. The method according to claim 10, wherein the cancer is selected from the group consisting of colorectal cancer, lung cancer, ovarian cancer, breast cancer, gall bladder cancer, prostatic cancer and uterine cervical cancer.

15. A therapeutic method for cancer in a mammal, which method comprises administering to the mammal an effective amount of an agent consisting of a polynucleotide comprising any ZNF143-binding nucleotide sequence selected from among the following nucleotide sequences, or an expression vector capable of expressing the polynucleotide, and a pharmaceutically acceptable carrier:

(1) the nucleotide sequence shown by SEQ ID NO: 4; and
(2) a nucleotide sequence having an identity of 60% or more to the nucleotide sequence shown by SEQ ID NO:

4, wherein the 4th, 5th, and 6th cytosines of the nucleotide sequence shown by SEQ ID NO: 4 are conserved, and wherein the 13th nucleotide is cytosine or guanine.

16. The method according to claim 15, wherein the cancer is selected from the group consisting of colorectal cancer, lung cancer, ovarian cancer, breast cancer, gall bladder cancer, prostatic cancer and uterine cervical cancer.

* * * * *